(12) United States Patent
Brown et al.

(10) Patent No.: US 12,182,595 B2
(45) Date of Patent: *Dec. 31, 2024

(54) VIRTUAL ASSISTANT FOCUSED USER INTERFACES

(71) Applicant: Verint Americas Inc., Alpharetta, GA (US)

(72) Inventors: Fred A. Brown, Colbert, WA (US); Tanya M. Miller, Colbert, WA (US); Richard Morris, San Francisco, CA (US)

(73) Assignee: Verint Americas Inc., Alpharetta, GA (US)

( * ) Notice: Subject to any disclaimer, the term of this patent is extended or adjusted under 35 U.S.C. 154(b) by 807 days.

This patent is subject to a terminal disclaimer.

(21) Appl. No.: 17/404,189

(22) Filed: Aug. 17, 2021

(65) Prior Publication Data

US 2021/0371528 A1 Dec. 2, 2021

Related U.S. Application Data

(60) Continuation of application No. 16/000,695, filed on Jun. 5, 2018, now Pat. No. 11,192,949, which is a
(Continued)

(51) Int. Cl.
*G10L 15/22* (2006.01)
*A61K 39/12* (2006.01)
(Continued)

(52) U.S. Cl.
CPC .............. *G06F 9/453* (2018.02); *A61K 39/12* (2013.01); *C07K 16/1063* (2013.01);
(Continued)

(58) Field of Classification Search
CPC ........ G06F 9/453; G06F 3/167; G06F 3/0488; G06F 3/0482; G06F 3/0486; G06Q 10/02;
(Continued)

(56) References Cited

U.S. PATENT DOCUMENTS 5,278,980 A 1/1994 Pedersen et al.
5,418,948 A 5/1995 Turtle
(Continued)

FOREIGN PATENT DOCUMENTS

BR 112014023539 B1 * 10/2022 ......... G06Q 30/0282
CA 2791277 A1 * 3/2013 ............. B60K 35/00
(Continued)

OTHER PUBLICATIONS

"5 wearable electronic phones", retrieved on Feb. 13, 2015 at <<http://limcorp.net/2009/5-wearable-electronic-phones>>, 2015, 12 pages.
(Continued)

*Primary Examiner* — Steven P Sax
(74) *Attorney, Agent, or Firm* — Meunier Carlin & Curfman LLC

(57) ABSTRACT

Conversation user interfaces that are configured for virtual assistant interaction may include contextual interface items that are based on contextual information. The contextual information may relate to a current or previous conversation between a user and a virtual assistant and/or may relate to other types of information, such as a location of a user, an orientation of a device, missing information, and so on. The conversation user interfaces may additionally, or alternatively, control an input mode based on contextual information, such as an inferred input mode of a user or a location of a user. Further, the conversation user interfaces may tag conversation items by saving the conversation items to a tray and/or associating the conversation items with indicators.

19 Claims, 17 Drawing Sheets

Related U.S. Application Data division of application No. 13/865,789, filed on Apr. 18, 2013, now Pat. No. 10,445,115.

(51) Int. Cl.

| | |
|---|---|
| *C07K 16/10* | (2006.01) |
| *C07K 16/28* | (2006.01) |
| *G06F 3/0488* | (2022.01) |
| *G06F 3/16* | (2006.01) |
| *G06F 9/451* | (2018.01) |
| *G06Q 10/02* | (2012.01) |
| *A61K 39/00* | (2006.01) |
| *G06F 3/0482* | (2013.01) |
| *G06F 3/0486* | (2013.01) |

(52) U.S. Cl.
CPC ........ *C07K 16/2812* (2013.01); *G06F 3/0488* (2013.01); *G06F 3/167* (2013.01); *G06Q 10/02* (2013.01); *G10L 15/22* (2013.01); *A61K 2039/5254* (2013.01); *A61K 2039/575* (2013.01); *C12N 2740/16122* (2013.01); *C12N 2740/16134* (2013.01); *G06F 3/0482* (2013.01); *G06F 3/0486* (2013.01)

(58) Field of Classification Search
CPC ......... G10L 15/06; G10L 15/18; G10L 15/22; G06N 20/00
See application file for complete search history.

(56) References Cited

U.S. PATENT DOCUMENTS

| | | |
|---|---|---|
| 5,535,120 A | 7/1996 | Chong et al. |
| 5,615,112 A | 3/1997 | Liu Sheng et al. |
| 5,677,835 A | 10/1997 | Carbonell et al. |
| 5,682,539 A | 10/1997 | Conrad et al. |
| 5,727,174 A | 3/1998 | Aparicio et al. |
| 6,012,053 A | 1/2000 | Pant et al. |
| 6,112,177 A | 8/2000 | Cosatto et al. |
| 6,144,938 A | 11/2000 | Surace et al. |
| 6,175,829 B1 | 1/2001 | Li et al. |
| 6,282,507 B1 | 8/2001 | Horiguchi et al. |
| 6,285,978 B1 | 9/2001 | Bernth et al. |
| 6,353,817 B1 | 3/2002 | Jacobs et al. |
| 6,388,665 B1 | 5/2002 | Linnett et al. |
| 6,396,951 B1 | 5/2002 | Grefenstette |
| 6,401,061 B1 | 6/2002 | Zieman |
| 6,658,627 B1 | 12/2003 | Gallup et al. |
| 6,661,418 B1 | 12/2003 | McMillan et al. |
| 6,757,362 B1 | 6/2004 | Cooper et al. |
| 6,826,540 B1 | 11/2004 | Plantec et al. |
| 6,829,603 B1 | 12/2004 | Chai et al. |
| 6,834,120 B1 | 12/2004 | LeClerc et al. |
| 6,987,514 B1 | 1/2006 | Beresin et al. |
| 6,999,932 B1 | 2/2006 | Zhou |
| 7,058,902 B2 | 6/2006 | Iwema et al. |
| 7,076,430 B1 | 7/2006 | Cosatto et al. |
| 7,194,483 B1 | 3/2007 | Mohan et al. |
| 7,263,493 B1 | 8/2007 | Provost et al. |
| 7,337,158 B2 | 2/2008 | Fratkina et al. |
| 7,426,697 B2 | 9/2008 | Holecek et al. |
| 7,483,829 B2 | 1/2009 | Murakami et al. |
| 7,536,413 B1 | 5/2009 | Mohan et al. |
| 7,539,656 B2 | 5/2009 | Fratkina et al. |
| 7,548,899 B1 | 6/2009 | Favero et al. |
| 7,558,792 B2 | 7/2009 | Bier |
| 7,599,831 B2 | 10/2009 | Ford |
| 7,610,382 B1 | 10/2009 | Siegel |
| 7,711,547 B2 | 5/2010 | Abir |
| 7,739,604 B1 | 6/2010 | Lyons et al. |
| 7,797,146 B2 | 9/2010 | Harless et al. |
| 7,818,183 B2 | 10/2010 | Schoenberg |
| 7,912,701 B1 | 3/2011 | Gray et al. |
| 7,970,663 B2 | 6/2011 | Ganz et al. |
| 8,160,979 B1 | 4/2012 | Evans et al. |
| 8,346,563 B1 | 1/2013 | Hjelm et al. |
| 8,352,266 B2 | 1/2013 | Farmaner et al. |
| 8,401,842 B1 | 3/2013 | Ginzburg et al. |
| 8,433,556 B2 | 4/2013 | Fraser et al. |
| 8,473,420 B2 | 6/2013 | Bohus |
| 8,510,276 B2 | 8/2013 | Haiby et al. |
| 8,519,963 B2 | 8/2013 | Kocienda et al. |
| 8,554,856 B2 | 10/2013 | Plotkin |
| 8,670,979 B2 | 3/2014 | Gruber et al. |
| 8,677,251 B2 | 3/2014 | Kwok et al. |
| 8,677,377 B2 | 3/2014 | Cheyer et al. |
| 8,731,929 B2 | 5/2014 | Kennewick et al. |
| 8,756,326 B1 | 6/2014 | Elberse et al. |
| 8,762,152 B2 | 6/2014 | Bennett et al. |
| 8,819,003 B2 | 8/2014 | Anick et al. |
| 8,930,191 B2 | 1/2015 | Gruber et al. |
| 8,942,986 B2 | 1/2015 | Cheyer et al. |
| 8,943,094 B2 | 1/2015 | Brown et al. |
| 9,117,447 B2 | 8/2015 | Gruber et al. |
| 9,202,171 B2 | 12/2015 | Kuhn |
| 9,495,331 B2 | 11/2016 | Govrin et al. |
| 9,501,741 B2 | 11/2016 | Cheyer et al. |
| 9,965,129 B2 | 5/2018 | Reiley et al. |
| 10,445,115 B2 * | 10/2019 | Brown ................. G06F 9/453 |
| 10,984,387 B2 * | 4/2021 | Gamon ............... G06Q 10/107 |
| 11,012,732 B2 * | 5/2021 | Daly .................... G10L 15/26 |
| 11,030,578 B2 * | 6/2021 | Robbins ............... G06Q 10/10 |
| 11,068,657 B2 * | 7/2021 | Motik .................. G06F 40/295 |
| 11,074,497 B2 * | 7/2021 | Ascari ................. G06N 7/01 |
| 11,301,345 B2 * | 4/2022 | Strode .................. G06F 3/165 |
| 11,393,461 B2 * | 7/2022 | Ganong, III ....... H04W 52/0261 |
| 11,544,750 B1 * | 1/2023 | Rothman ............ G06F 16/958 |
| 11,587,172 B1 * | 2/2023 | Guzman ............. G06Q 40/08 |
| 11,627,173 B2 * | 4/2023 | Wiklund ............. H04L 65/765 |
| | | 709/224 |
| 2001/0000356 A1 | 4/2001 | Woods |
| 2001/0033298 A1 | 10/2001 | Slotznick |
| 2001/0044751 A1 | 11/2001 | Pugliese et al. |
| 2001/0049688 A1 | 12/2001 | Fratkina et al. |
| 2001/0053968 A1 | 12/2001 | Galitsky et al. |
| 2002/0008716 A1 | 1/2002 | Colburn et al. |
| 2002/0032591 A1 | 3/2002 | Mahaffy et al. |
| 2002/0123994 A1 | 9/2002 | Schabes et al. |
| 2002/0129031 A1 | 9/2002 | Lau et al. |
| 2002/0198885 A1 | 12/2002 | Streepy |
| 2003/0004908 A1 | 1/2003 | Linthicum et al. |
| 2003/0041307 A1 | 2/2003 | Park |
| 2003/0061029 A1 | 3/2003 | Shaket |
| 2003/0088547 A1 | 5/2003 | Hammond |
| 2003/0126089 A1 | 7/2003 | Fukuoka et al. |
| 2003/0126090 A1 | 7/2003 | Fukuoka et al. |
| 2003/0134632 A1 | 7/2003 | Loughran |
| 2003/0142829 A1 | 7/2003 | Avigni |
| 2003/0212544 A1 | 11/2003 | Acero et al. |
| 2004/0107088 A1 | 6/2004 | Budzinski |
| 2004/0141013 A1 | 7/2004 | Alcazar et al. |
| 2004/0186705 A1 | 9/2004 | Morgan et al. |
| 2005/0027524 A1 | 2/2005 | Wu et al. |
| 2005/0027694 A1 | 2/2005 | Sauermann |
| 2005/0054381 A1 | 3/2005 | Lee et al. |
| 2005/0120276 A1 | 6/2005 | Kolawa et al. |
| 2006/0004826 A1 | 1/2006 | Zartler et al. |
| 2006/0020466 A1 | 1/2006 | Cousineau et al. |
| 2006/0036430 A1 | 2/2006 | Hu |
| 2006/0037076 A1 | 2/2006 | Roy |
| 2006/0047632 A1 | 3/2006 | Zhang |
| 2006/0067352 A1 | 3/2006 | John et al. |
| 2006/0074689 A1 | 4/2006 | Cosatto et al. |
| 2006/0074831 A1 | 4/2006 | Hyder et al. |
| 2006/0080107 A1 | 4/2006 | Hill et al. |
| 2006/0092978 A1 | 5/2006 | John et al. |
| 2006/0161414 A1 | 7/2006 | Carignano et al. |
| 2006/0206483 A1 | 9/2006 | Knepper et al. |
| 2006/0230410 A1 | 10/2006 | Kurganov et al. |
| 2006/0253427 A1 | 11/2006 | Wu |
| 2007/0043687 A1 | 2/2007 | Bodart et al. |
| 2007/0100790 A1 | 5/2007 | Cheyer et al. |
| 2007/0106670 A1 | 5/2007 | Yoakum et al. |

(56) References Cited

U.S. PATENT DOCUMENTS

| | | |
|---|---|---|
| 2007/0130112 A1 | 6/2007 | Lin |
| 2007/0134631 A1 | 6/2007 | Hardy et al. |
| 2007/0156677 A1 | 7/2007 | Szabo |
| 2007/0185702 A1 | 8/2007 | Harney et al. |
| 2007/0197296 A1 | 8/2007 | Lee |
| 2007/0265533 A1 | 11/2007 | Tran |
| 2007/0294229 A1 | 12/2007 | Au |
| 2008/0005158 A1 | 1/2008 | Zartler et al. |
| 2008/0010268 A1 | 1/2008 | Liao et al. |
| 2008/0016040 A1 | 1/2008 | Jones et al. |
| 2008/0036756 A1 | 2/2008 | Gaos et al. |
| 2008/0091406 A1 | 4/2008 | Baldwin et al. |
| 2008/0096533 A1 | 4/2008 | Manfredi et al. |
| 2008/0133444 A1 | 6/2008 | Gao et al. |
| 2008/0153474 A1 | 6/2008 | Scott |
| 2008/0162498 A1 | 7/2008 | Omoigui |
| 2008/0222734 A1 | 9/2008 | Redlich et al. |
| 2008/0235604 A1 | 9/2008 | Eber |
| 2008/0305815 A1 | 12/2008 | McDonough |
| 2009/0006525 A1 | 1/2009 | Moore |
| 2009/0030767 A1 | 1/2009 | Morris et al. |
| 2009/0030800 A1 | 1/2009 | Grois |
| 2009/0060162 A1 | 3/2009 | Lachhiramka |
| 2009/0063427 A1 | 3/2009 | Zuta et al. |
| 2009/0070103 A1 | 3/2009 | Beggelman et al. |
| 2009/0077488 A1 | 3/2009 | Ording |
| 2009/0089100 A1 | 4/2009 | Nenov et al. |
| 2009/0119095 A1 | 5/2009 | Beggelman et al. |
| 2009/0119587 A1 | 5/2009 | Allen |
| 2009/0157386 A1 | 6/2009 | Zhou |
| 2009/0171720 A1 | 7/2009 | Crook et al. |
| 2009/0171923 A1 | 7/2009 | Nash et al. |
| 2009/0182702 A1 | 7/2009 | Miller |
| 2009/0204677 A1 | 8/2009 | Michaelis et al. |
| 2009/0216691 A1 | 8/2009 | Borzestowski et al. |
| 2009/0225041 A1 | 9/2009 | Kida et al. |
| 2009/0227223 A1 | 9/2009 | Jenkins |
| 2009/0228264 A1 | 9/2009 | Williams et al. |
| 2009/0228325 A1 | 9/2009 | Simmons et al. |
| 2009/0235356 A1 | 9/2009 | Jensen et al. |
| 2009/0248399 A1 | 10/2009 | Au |
| 2009/0271205 A1 | 10/2009 | Finn et al. |
| 2010/0005122 A1 | 1/2010 | Jackson |
| 2010/0030549 A1 | 2/2010 | Lee et al. |
| 2010/0050237 A1 | 2/2010 | Bokor et al. |
| 2010/0070448 A1 | 3/2010 | Omoigui |
| 2010/0070871 A1 | 3/2010 | Liesche |
| 2010/0153398 A1 | 6/2010 | Miller et al. |
| 2010/0169336 A1 | 7/2010 | Eckhoff-Hornback et al. |
| 2010/0226490 A1 | 9/2010 | Schultz et al. |
| 2010/0235808 A1 | 9/2010 | Dayan et al. |
| 2010/0281012 A1 | 11/2010 | Imig |
| 2010/0287059 A1 | 11/2010 | McCoy et al. |
| 2010/0312547 A1 | 12/2010 | Van Os et al. |
| 2011/0004841 A1 | 1/2011 | Gildred et al. |
| 2011/0071819 A1 | 3/2011 | Miller et al. |
| 2011/0078105 A1 | 3/2011 | Wallace |
| 2011/0119196 A1 | 5/2011 | Ventura |
| 2011/0179126 A1 | 7/2011 | Wetherell et al. |
| 2011/0213642 A1 | 9/2011 | Makar et al. |
| 2011/0288947 A1 | 11/2011 | Biran |
| 2011/0301982 A1 | 12/2011 | Green et al. |
| 2011/0307245 A1 | 12/2011 | Hanneman et al. |
| 2012/0022872 A1 | 1/2012 | Gruber et al. |
| 2012/0030553 A1 | 2/2012 | Delpha et al. |
| 2012/0041903 A1 | 2/2012 | Beilby et al. |
| 2012/0078891 A1 | 3/2012 | Brown et al. |
| 2012/0110473 A1 | 5/2012 | Tseng |
| 2012/0117005 A1 | 5/2012 | Spivack |
| 2012/0221502 A1 | 8/2012 | Jerram et al. |
| 2012/0245926 A1 | 9/2012 | Montyne et al. |
| 2012/0253825 A1 | 10/2012 | Di Fabbrizio |
| 2012/0266093 A1 | 10/2012 | Park et al. |
| 2012/0284040 A1 | 11/2012 | Dupin |
| 2012/0311541 A1 | 12/2012 | Bullard et al. |
| 2013/0017523 A1 | 1/2013 | Barborak |
| 2013/0031476 A1 | 1/2013 | Coin et al. |
| 2013/0046149 A1 | 2/2013 | Gettelman et al. |
| 2013/0117713 A1 | 5/2013 | Bauder et al. |
| 2013/0152092 A1 | 6/2013 | Yadgar |
| 2013/0204813 A1 | 8/2013 | Master et al. |
| 2013/0205975 A1 | 8/2013 | Williams |
| 2013/0254139 A1 | 9/2013 | Lei |
| 2013/0258040 A1 | 10/2013 | Kaytaz et al. |
| 2013/0262467 A1 | 10/2013 | Zhang et al. |
| 2013/0275875 A1 | 10/2013 | Gruber et al. |
| 2013/0282709 A1 | 10/2013 | Zhu et al. |
| 2013/0283168 A1 | 10/2013 | Brown et al. |
| 2013/0317848 A1 | 11/2013 | Savin |
| 2014/0019303 A1 | 1/2014 | Argue et al. |
| 2014/0029734 A1 | 1/2014 | Kim et al. |
| 2014/0040748 A1 | 2/2014 | Lemay et al. |
| 2014/0045470 A1 | 2/2014 | Bridge et al. |
| 2014/0046792 A1 | 2/2014 | Ganesan |
| 2014/0047001 A1 | 2/2014 | Phillips et al. |
| 2014/0053102 A1 | 2/2014 | Lee et al. |
| 2014/0066105 A1 | 3/2014 | Bridge et al. |
| 2014/0074454 A1 | 3/2014 | Brown |
| 2014/0098948 A1 | 4/2014 | Kulkarni et al. |
| 2014/0115456 A1 | 4/2014 | Whit et al. |
| 2014/0164476 A1 | 6/2014 | Thomson |
| 2014/0164508 A1 | 6/2014 | Lynch et al. |
| 2014/0181741 A1 | 6/2014 | Apacible et al. |
| 2014/0195926 A1 | 7/2014 | Hussain |
| 2014/0201675 A1 | 7/2014 | Joo et al. |
| 2014/0244266 A1 | 8/2014 | Brown et al. |
| 2014/0244712 A1 | 8/2014 | Walters et al. |
| 2014/0245140 A1 | 8/2014 | Brown et al. |
| 2014/0258503 A1 | 9/2014 | Tong et al. |
| 2014/0270109 A1 | 9/2014 | Riahi et al. |
| 2014/0280490 A1 | 9/2014 | Artun |
| 2014/0282109 A1 | 9/2014 | Wenger et al. |
| 2014/0297284 A1 | 10/2014 | Gruber et al. |
| 2014/0310005 A1 | 10/2014 | Brown et al. |
| 2014/0337048 A1 | 11/2014 | Brown et al. |
| 2014/0343924 A1 | 11/2014 | Brown et al. |
| 2014/0343928 A1 | 11/2014 | Brown et al. |
| 2014/0365223 A1 | 12/2014 | Brown et al. |
| 2014/0365407 A1 | 12/2014 | Brown et al. |
| 2015/0066817 A1 | 3/2015 | Slayton et al. |
| 2015/0185996 A1 | 7/2015 | Brown et al. |
| 2015/0186154 A1 | 7/2015 | Brown et al. |
| 2015/0186155 A1 | 7/2015 | Brown et al. |
| 2015/0186156 A1 | 7/2015 | Brown et al. |
| 2016/0012186 A1 | 1/2016 | Zasowski et al. |
| 2016/0110071 A1 | 4/2016 | Brown et al. |
| 2017/0032027 A1 | 2/2017 | Mauro et al. |
| 2017/0132220 A1 | 5/2017 | Brown et al. |
| 2017/0277993 A1 | 9/2017 | Beaver et al. |
| 2019/0057698 A1 | 2/2019 | Raanani et al. |

FOREIGN PATENT DOCUMENTS

| | | | | |
|---|---|---|---|---|
| CA | 3068661 C | * | 2/2022 | ............ G06F 16/36 |
| CA | 3041557 C | * | 3/2022 | ....... G06F 16/24573 |
| CA | 3023918 C | * | 11/2022 | ............ B60K 35/00 |
| CN | 103051669 | | 4/2013 | |
| EP | 2610724 B1 | * | 1/2022 | ........... G06F 3/0481 |
| EP | 2238777 B1 | * | 10/2023 | ......... H04L 63/0281 |
| WO | 2011/088053 | | 7/2011 | |

OTHER PUBLICATIONS

Adamic, L., et al., "How to search a social network," Social Networks, vol. 27, Issue 3, 2005, pp. 187-203.

AppleKeynotes, "Apple Special Event 2011—Siri Introduction", YouTube, retrieved on Oct. 21, 2016 at http://www.youtube.com/watch?y=agzlTz35QQ, 2013, 1 page.

"AskJennMediaCoverage," retrieved on Nov. 12, 2014, 76 pages.

"CALO", retrieved on Nov. 15, 2017 at http://en.wikipedia.org/wiki/CALO, 2003, 5 pages.

Cassell, J., et al., "Embodied Conversational Agents," MIT Press, 2000, pp. 272 and 275.

(56) References Cited

OTHER PUBLICATIONS

"Frost & Sullivan Commends Next IT for Leading the Virtual Agent Applications Industry in Competitive Strategy Innovation," 2014, 5 pages.
Guzzoni, D., et al., "Modeling Human-Agent Interaction with Active Ontologies," Spring 2007 AAAI Symposium, 2007, 8 pages.
Hirschman, L., et al., "Natural language question answering: the view from here," Natural Language Engineering, vol. 7, No. 4, 2001, pp. 275-300.
Krahmer, E., et al., "Problem Spotting in Human-Machine Interaction," IPO, Center for Research on User-System Interaction, Sixth European Conference on Speech Communication and Technology, 1999, 4 pages.
Langkilde, I., et al., "Automatic Prediction of Problematic Human-Computer Dialogues in 'How May I Help You?,'" AT&T Labs Research, 1999, 5 pages.
"Meet Jenn, Your Virtual Assistant at alaskaair.com," retrieved on Apr. 13, 2015 at http://www.alaskaair.com/content/about-us/site-info/ask-jenn.aspx, 2013, 1 page.
"Meet Julia—TAM Airlines' most famous new hire," Case Study, 2015, 2 pages.
Pandorabots Inc. "AIML Targeting: Supervised Learning for Bots," uploaded on Oct. 29, 2009 at https://www.youtube.com/watch?v=aGe30NTVDOK.
"SGT STAR Wins Intelligent Assistant Award," PRWEB Online Visibility from Vocus, Sep. 24, 2014, 2 pages.
"The Army's Robot Recruiter," Transcript from New York Public Radio, retrieved on Jan. 20, 2015 at http://www.onthemedia.org/story/armys-robot-recruiter-aug/transcript, Aug. 8, 2014, 3 pages.
"Undercover Virtual Agent Article," KOMO News, retrieved Nov. 12, 2014, 2 pages.
Walker, M., et al., "Learning to Predict Problematic Situations in a Spoken Dialogue System: Experiments with How May I Help You?", AT&T Labs Research, NAACL 2000 Proceedings of the 1st North American chapter of the Association for Computational Linguistics conference, Seattle, Washington, Apr. 29-May 4, 2000, 8 pages.
"With Alme, Alaska Airlines soars", Case Study, retrieved on Apr. 10, 2015 at http://www.nextit.com/media/downloads/Case-study-Alaska-Air.pdf, 2013, 3 pages.
Extended Search Report, dated Mar. 17, 2017, received in connection with corresponding EP Patent Application No. 14785575.3.
Supplementary Search Report, dated Oct. 31, 2016, received in connection with corresponding EP Patent Application No. 14785575.3.
International Search Report and Written Opinion, dated Nov. 12, 2014, received in connection with corresponding International Patent Application No. PCT/US2014/031047.
Ramabhadran, S., et al., Prefix Hash Tree: An Indexing Data Structure Over Distributed Hash Tables, Proceedings of the $23^{rd}$ ACM Symposium on Principles of Distributed Computing, St. John's, vol. 37, Jul. 2004, 10 pages.
Ratnasamy, S., et al., "A Scalable Content-Addressable Network," Proceedings of the 2001 Conference on Applications, Technologies, Architectures, and Protocols for Computer Communications, Aug. 27, 2001, pp. 161-172.

\* cited by examiner

VIRTUAL ASSISTANT FOCUSED USER INTERFACES

CROSS-REFERENCE TO RELATED APPLICATIONS

This application is a continuation of U.S. patent application Ser. No. 16/600,695, filed Oct. 14, 2019, which is a divisional of U.S. patent application Ser. No. 13/865,789, filed Apr. 18, 2013. The contents of both applications are incorporated herein by reference in their entirety.

BACKGROUND

A growing number of people are using smart devices, such as smart phones, tablet computers, laptop computers, and so on, to perform a variety of functionality. In many instances, the users interact with their devices through a virtual assistant. The virtual assistant may communicate with a user to perform a desired task, such as searching for content, checking into a flight, setting a calendar appointment, and so on. As the virtual assistant interacts with the user, information may be displayed that is irrelevant to the interaction and/or visually overwhelming. Accordingly, there is an increasing need to interface with a virtual assistant in an efficient manner, particularly when a mobile device is used that includes limited display space.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Figure 1:
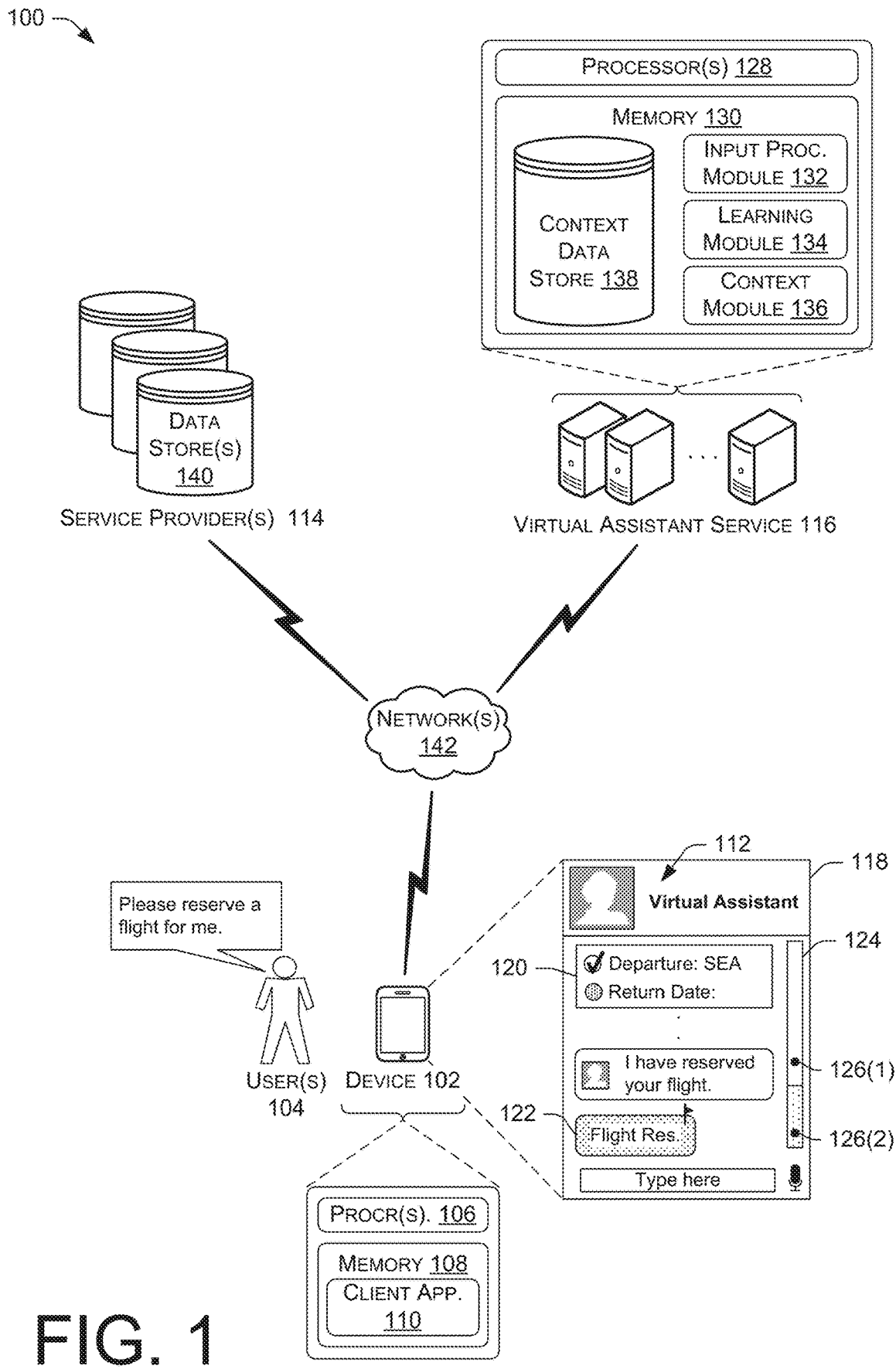
FIG. 1 illustrates an example architecture in which techniques described herein may be implemented.

This disclosure describes, in part, virtual assistant user interfaces that include contextual interface items. In some instances, a conversation user interface may be displayed on a smart device to enable an interaction between a user and a virtual assistant. The conversation user interface may display interface items that are based on contextual information (e.g., conversation history, user preferences, user location, missing information, preferred input mode, etc.). The interface items may be presented at appropriate times in the conversation and/or in a manner that does not visually overwhelm the user.

In one example, the conversation user interface may display an information item that represents information that has been shared during a conversation between the virtual assistant and the user. The information item may represent the shared information in a condensed format (e.g., through an icon) and/or may be displayed when a particular event has occurred. For instance, if the virtual assistant and/or the user share various pieces of information to reserve a flight (e.g., departure city, arrival city, preferred departure time, amount to be paid, etc.), the conversation user interface may display an icon representing the shared information when the flight has been reserved. The user may select the icon to view the flight reservation information or may continue on in the conversation. By presenting the icon, the conversation user interface may represent information that has particular relevance to the conversation in a condensed manner. For example, the icon may represent a discrete task or a discrete sub-part of a task. This may avoid overwhelming the user with relatively large amounts of information in the conversation user interface.

In another example, the conversation user interface may display a mixed response information item as a response to input from a user that is open to multiple interpretations. The mixed response information item may include information that satisfies one of the interpretations and a selectable item to perform a task that satisfies another of the interpretations. For instance, if the user states "flight 101," the virtual assistant may provide status information of flight 101 (e.g., "flight 101 is on time") and provide a selectable item to obtain a boarding pass for flight 101.

In yet another example, the conversation user interface may display an information item that indicates what information has been obtained and what information is missing to perform a task. Here, a user may request that the virtual assistant perform a task that requires a particular amount of information. If the virtual assistant is only able to obtain a portion of the information, either through input from the user or otherwise, then the conversation user interface may display an information item that indicates what information has been obtained and what information is missing. The user may then input the missing information. This may allow the virtual assistant to avoid multiple inquiries to the user to obtain the missing information and/or allow the user to view the virtual assistant's progress toward obtaining information.

In a further example, the conversation user interface may provide a movable interface item to provide user input for a task to be performed by the virtual assistant. The user may select the movable interface item and drag the item to another interface item to provide the user input. Based on the user input, the virtual assistant may perform the task. For example, to answer an inquiry "how many bags do you want to check," the user may select an icon labeled "bags to check" and drag the icon onto one of multiple option icons labeled "0," "1," and "2+," respectively. The virtual assistant may then check-in the user with the specified number of bags.

This disclosure also describes virtual assistant user interfaces that control an input mode of the interfaces based on contextual information. For example, the virtual assistant may determine that the user has previously used speech input more than a particular number of times during previous conversations with the virtual assistant. Based on this determination, when the conversation user interface is initialized, a microphone may be enabled as a primary mode of input (e.g., a keyboard or text input box may be hidden). In another example, the virtual assistant may determine that the user is located in a meeting and control the conversation user interface to present a keyboard as a primary mode of input.

This disclosure also describes virtual assistant user interfaces for tagging conversation items. In some instances, a conversation item may be tagged by saving the conversation item to a tray. The tray may be accessed by particular user input, such as swiping to the side or selecting an icon. Alternatively, or additionally, a conversation item may be tagged by associating the conversation item with a displayable flag or other indicator. In either instance, when a conversation item is tagged, the conversation user interface may display a timeline bar with a marking to indicate a location of the tagged conversation item with respect to the entire conversation. When the user selects the marking, the conversation user interface may return to the location of the tagged conversation item. This may allow the user to efficiently locate conversation items that may be of particular interest to the user.

Although many examples described herein relate to an airline context, the techniques described herein may be implemented within any context. Further, although many examples are described herein in the context of visually displayed user interfaces, these techniques may, in some instances, be implemented with audible user interfaces (e.g., presented through a speaker of a smart device) or other contexts.

This brief introduction is provided for the reader's convenience and is not intended to limit the scope of the claims, nor the proceeding sections. Furthermore, the techniques described in detail below may be implemented in a number of ways and in a number of contexts. One example implementation and context is provided with reference to the following figures, as described below in more detail. It is to be appreciated, however, that the following implementation and context is but one of many.

Example Architecture

FIG. 1 illustrates an example architecture 100 in which techniques described herein may be implemented. The architecture 100 includes a smart device 102 configured to interact with one or more users 104 (hereinafter the user 104) and perform other processing discussed herein. The smart device 102 may comprise any type of computing device that is configured to perform an operation. For example, the smart device 102 may be implemented as a laptop computer, a desktop computer, a server, a smart phone, an electronic reader device, a mobile handset, a personal digital assistant (PDA), a portable navigation device, a portable gaming device, a tablet computer, a watch, a portable media player, a television, a set-top box, a computer system in a car, an appliance, a camera, a robot, a hologram system, a security system, a home-based computer system (e.g., intercom system, home media system, etc.), a projector, an automated teller machine (ATM), a pair of glass with computing capabilities, and so on.

The smart device 102 may be equipped with one or more processors 106, memory 108, a display(s), a microphone(s), a speaker(s), a camera(s), a sensor(s), and a network interface(s). The sensor(s) may include an accelerometer, compass, gyroscope, magnetometer, Global Positioning System (GPS), olfactory sensor (e.g., for smell), or other sensor. In some instances, the display(s) is implemented as one or more touch screens. The camera(s) may include a front facing camera and/or a rear facing camera. The display(s), microphone(s), speaker(s), camera(s), and/or sensor(s) may be configured to receive user input, such as gesture input (e.g., through the camera), touch input, audio or speech input, and so on, and/or may be configured to output content, such as audio, images, video, and so on.

The memory 108 may include a client application 110 (e.g., module) configured to interface with the user 104. The client application 110 may receive any type of input from the user 104, such as audio or speech, text, touch, or gesture input received through a sensor of the smart device 102. The client application 110 may also provide any type of response, such as audio, text, interface items (e.g., icons, buttons, menu elements, etc.), and so on. In some implementations, the client application 110 is implemented as, or in association with, a mobile application, a browser (e.g., mobile browser), and so on.

The client application 110 may be implemented as, or in conjunction with, a virtual assistant 112 (e.g., an intelligent personal assistant). A "virtual assistant" may generally act as an interface between end users and information of one or more service providers 114 (hereinafter the service provider 114), information of the smart device 102, information of a virtual assistant service 116, or any type of information. For example, in response to input from the user 104, the virtual assistant 112 may access content items stored on the service provider 114 to formulate a response to the user 104. In some instances, the virtual assistant 112 may embody a human-like persona and/or artificial intelligence (AI). For example, the virtual assistant 112 may be represented by an image or avatar that is displayed on the smart device 102. An avatar may comprise an animated character that may take on any number of shapes and appearances, and/or resemble a human talking to a user. In some instances, the avatar may be arranged as a representative of the service provider 114, while in other instances the avatar may be a dedicated personal assistant to a user.

The virtual assistant 112 may interface with the user through a conversation user interface 118. The conversation user interface 118 may provide conversation items representing information from the virtual assistant 112 and/or information from the user 104. For example, in response to a query from the user 104 to "find the nearest restaurant," the conversation user interface 118 may display a dialog representation of the user's query and a response item of the virtual assistant 112 that identifies the nearest restaurant to the user 104. A conversation item may comprise an icon (e.g., selectable or non-selectable), a menu item (e.g., drop down menu, radio control, etc.), text, a link, audio, video, or any other type of information.

A conversation item may be associated with one or more pieces of contextual information, such as a conversation history, a user preference, and so on. In one example, as illustrated in FIG. 1, the conversation user interface 118 may display a conversation item 120 that indicates what information has been obtained from the user 104 and what information is missing to perform a task (e.g., a check mark indicator indicates that the departure city has been identified, while the stippling indicator indicates that the return date is missing). In another example, as also illustrated in FIG. 1, the conversation user interface 118 may display a conversation item 122 that represents information obtained for reserving a flight. Here, the user 104 and virtual assistant 112 have exchanged various pieces of information to reserve a flight (e.g., flight amount, departure date, return date, flight number, airlines, etc.). Upon reserving the flight, the conversation item 122 may be displayed to represent the exchanged information and/or other information for the reservation (e.g., a total amount paid for a reserved flight, a confirmation number of a reserved flight, etc.). Further example contextual conversation items are discussed below.

In addition to conversation items, the conversation user interface 118 may include other interface items. For example, the conversation user interface 118 may include a microphone icon for speech input, a text box to input text, a keyboard (e.g., touch screen keyboard), other input icons, and so on. In some instances, the conversation user interface 118 includes a timeline bar 124 that displays position of a conversation. The timeline bar 124 may include indicators 126(1)-(2) (e.g., markings) to indicate locations of conversation items that have been tagged. In the example conversation user interface 118 of FIG. 1, the "Flight Reservation" conversation item 122 is tagged, as indicated by the flag. The indicator 126(2) is presented in the timeline bar 124 to indicate this tagging.

In some instances, the conversation user interface 118 may adapt an input mode for a user based on contextual information. For example, if a user primarily uses text input, the conversation user interface 118 may present a touch keyboard when the interface 118 is accessed. In another example, if a user is located in a car, the conversation user interface 118 may enable a microphone (e.g., listen for audio through the microphone). Additionally, or alternatively, the conversation user interface 118 may include functionality to tag a conversation item, as discussed in further detail below.

Although the conversation user interface 118 has been described as being associated with the smart device 102, in other examples the conversation user interface 118 is associated with the service provider 114 and/or the virtual assistant service 116. In one instance, the interface 118 is displayed through an online site of the service provider 114, such as when the user navigates to the online site. Here, the interface 118 may include a virtual assistant that embodies characteristics of the service provider 114, such as a flight attendant for an online airline site.

In many instances, the virtual assistant 112 operates in cooperation with the virtual assistant service 116. That is, one or more functions of the virtual assistant 112 may be performed by the virtual assistant service 116. The virtual assistant service 116 may generally provide one or more services, such as speech recognition, response formulation, context analysis, user characteristic analysis, and so on. For instance, input received at the smart device 102 from a user may be sent to the virtual assistant service 116 to interpret the speech and formulate a response to the input. The response may include outputting content (e.g., outputting audio (an audible answer), video, an image, text, a hyperlink, etc.), performing an action related to content (e.g., logging a user into a site, navigating to a web site, upgrading a user's seat assignment, purchasing an item, etc.), and so on. In some instances, a response may be addressed to or otherwise tailored to a particular user (e.g., "Yes, John, as a Gold Customer you are entitled to a seat upgrade, and I have provided some links below that may be of interest to you . . . "). After formulating a response, the virtual assistant service 116 may provide the response to the smart device 102 to be output and/or to cause the smart device 102 to perform an action. As such, the virtual assistant service 116 may operate as a "back-end" resource.

The virtual assistant service 116 may include one or more computing devices. The one or more computing devices may be implemented as one or more desktop computers, laptop computers, servers, and the like. The one or more computing devices may be configured in a cluster, data center, cloud computing environment, or a combination thereof. In one example, the virtual assistant service 116 provides cloud computing resources, including computational resources, storage resources, and the like, that operate remotely to the smart device 102.

The one or more computing devices of the virtual assistant service 116 may include one or more processors 128 and memory 130. The memory 130 may include software functionality configured as one or more "modules." The term "module" is intended to represent example divisions of the software for purposes of discussion, and is not intended to represent any type of requirement or required method, manner or necessary organization. Accordingly, while various "modules" are discussed, their functionality and/or similar functionality could be arranged differently (e.g., combined into a fewer number of modules, broken into a larger number of modules, etc.). As illustrated in FIG. 1, the memory 130 includes an input processing module 132, a learning module 134, and a context module 136.

The input processing module 132 may perform various techniques to process input received from a user. If, for example, the input is speech input, the input processing module 132 may perform speech recognition techniques to convert the input into a format that is understandable by a computing device, such as text. Additionally, or alternatively, the input processing module 132 may utilize Natural Language Processing (NLP) to interpret or derive a meaning and/or concept of the input. The speech recognition and/or NLP techniques may include known or new techniques.

The learning module 134 may be configured to observe user activity and attempt to learn characteristics about a user. The learning module 134 may learn any number of characteristics about the user over time, such as user preferences (e.g., likes and dislikes), track patterns (e.g., user normally reads the news starting with the sports, followed by the business section, followed by the world news), behaviors (e.g., listens to music in the morning and watches movies at night, speaks with an accent that might impact language models, prefers own music collection rather than looking for new music in the cloud, etc.), and so on. To observe user activity and learn a characteristic, the learning module 134 may access a user profile, track a pattern, monitor navigation of the user, and so on. Each of these learned characteristics may be useful to provide context that may be utilized to interpret input received from the user.

As an example of the learning, consider a scenario where a user incorrectly inputs "Cobo" or a speech recognition system incorrectly recognized the user input as "Cobo". Once the user corrects this to say "Cabo", the learning module 134 can record this correction from "Cobo" to "Cabo" in the event that a similar situation arises in the future. Thus, when the user next speaks the phrase "Cabo San Lucas", and even though the speech recognition might recognize the user input as "Cobo", the virtual assistant service 116 will use the learned correction and make a new assumption that the user means "Cabo" and respond accordingly. As another example, if a user routinely asks for the movie "Crazy", the learning module 134 will learn over time that this is the user preference and make this assumption. Hence, in the future, when the user says "Play Crazy", the virtual assistant service 116 will make a different initial assumption to begin play of the movie, rather than the original assumption of the song "Crazy" by Willie Nelson.

The context module 136 may be configured to identify (e.g., determine) one or more pieces of contextual information. The context module 136 may take into account contextual information when determining an intent or meaning of a user's query. In addition, after identifying the user's intent with use of the context, the context module 136 may again take this context into account when determining a response or reply to provide back to the user. In some instances, the context module 136 may take the same pieces of context into account when identifying the intent and the response, while in other instances the techniques may take into account different pieces of context. In some instances, by taking context into account in at least these locations, a response may be provided to a user that more closely emulates human-to-human interaction, in comparison to traditional techniques for identifying virtual assistant responses.

Further, in some instances the context module 136 may take into account contextual information when no query has been received from a user. For example, the context module 136 may monitor a location of a user to determine when the user has arrived at a particular location. Upon arrival at the particular location, information may be presented that is relevant to that location (e.g., provide a boarding pass upon arrival at an airport). In this example, the monitoring may occur in the background (e.g., when the user is not interacting with a virtual assistant).

Generally, contextual information may comprise any type of information that aids in understanding the meaning of a query of a user and/or in formulating a response for a virtual assistant or other information provided by a virtual assistant. In some instances, contextual information is expressed as a value of one or more variables, such as whether or not a user has signed in with a site (e.g., "is_signed_in=true" or "is_signed_in=false"). Contextual information may be stored in a context data store 138. Example, non-limiting pieces of contextual information may include:

interaction information between a user and a virtual assistant, either during the current session or during a previous session(s) (e.g., a conversation history (input and/or response) during a current or previous conversation session, a navigation history of the user during a conversation session prior to the user providing a query to the virtual assistant, etc.);

input history indicating one or more input modes that a user has used to interact with a user interface;

what type of input mode the user prefers to interact with a virtual assistant (e.g., input mode—whether the user prefers to submit a query textually, using voice input, touch input, gesture input, etc.), the preferred input mode may be inferred from previous interactions, explicit input of the user, profile information, etc.;

calendar information describing one or more events of a user (e.g., a scheduled flight, a work meeting, etc.);

a location of a cursor on a site when a user provides input to a virtual assistant;

a time of day or date on which a user provides input to a virtual assistant;

an age or gender of a user;

a location of a user (e.g., a geo-location of the user associated with a device through which the user provides a query, location based on network information, address of the user, etc.);

sensor information obtained from a sensor of a device with which a user is interacting (e.g., a geo-location, environmental data including background noise or video/audio from a surrounding of the device, etc.);

a device type from which a user interacts with a virtual assistant (e.g., a mobile device, a desktop computer, game system, etc.);

an orientation of a device which a user is using to interact with a virtual assistant (e.g., landscape or portrait);

a communication channel which a device of a user uses to interface with the virtual assistant service (e.g., wireless network, wired network, etc.);

a language associated with a user (e.g., a language of a query submitted by the user);

how an interaction with a virtual assistant is initiated (e.g., via user selection of a link or graphic, via the virtual assistant proactively engaging a user, etc.);

how a user has been communicating recently (e.g., via text messaging, via email, etc.);

information derived from a user's location (e.g., current, forecasted, or past weather at a location, major sports teams at the location, nearby restaurants, etc.);

current topics of interest, either to a user or generally (e.g., trending micro-blog or blog topics, current news, recent micro-blog or blog posts made by the user, etc.);

whether or not a user has signed-in with a site of a service provider (e.g., with a user name and password);

a status of a user with a service provider (e.g., based on miles flown, a type of membership of the user, a type of subscription purchased by the user, etc.);

a page of a site from which a user provides a query to a virtual assistant;

how long a user has remained on a page of a site from which the user provides a query to the virtual assistant;

social media information (e.g., posts or other content posted to a social networking site or blog);

a user preference (e.g., a seat preference, a home airport, a preference of whether schedule or price is important to a user, a type of weather a user enjoys, types of items acquired by a user and identifying information for those items, types of stock a user owns or sold, etc.);

user profile information (e.g., information identifying friends/family of a user, information identifying where a user works or lives, information identifying a car a user owns, etc.);

any characteristic of a user.

Although the modules 132-136 are illustrated as being included in the virtual assistant service 116, in some instances one or more of these modules may be included in the smart device 102 or elsewhere. As such, in some examples the virtual assistant service 116 may be eliminated entirely, such as in the case when all processing is performed locally at the smart device 102 (e.g., the smart device 102 operates independently).

The memory 108 and/or 130 (as well as all other memory described herein) may include one or a combination of computer storage media. Computer storage media includes volatile and non-volatile, removable and non-removable media implemented in any method or technology for storage of information, such as computer readable instructions, data structures, program modules, or other data. Computer storage media includes, but is not limited to, phase change memory (PRAM), static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transmission medium that can be used to store information for access by a computing device. As defined herein, computer storage media does not include communication media, such as modulated data signals and carrier waves. As such, computer storage media is non-transitory media.

The service provider 114 may include one or more data stores 140 for storing content items. For example, the service provider 114 may include a mobile web data store, a smart web data store, an information and content data store, a content management service (CMS) data store, and so on. A mobile web data store may store content items that are designed to be viewed on a mobile device, such as a mobile telephone, tablet device, etc. Meanwhile, a web data store includes content items that are generally designed to be viewed on a device that includes a relatively large display, such as a desktop computer. An information and content data store may include content items associated with an application, content items from a data base, and so on. A CMS data store may include content items providing information about a user, such as a user preference, user profile information, information identifying offers that are configured to a user based on profile and purchase preferences, etc. As such, the service provider 114 may include content items from any type of source. Although the one or more data stores 140 are illustrated as included in the service provider 114, the one or more data stores 140 may alternatively, or additionally, be included in the virtual assistant service 116 and/or the smart device 102.

The architecture 100 may also include one or more networks 142 to enable the smart device 102, the virtual assistant service 116, and/or the service provider 114 to communicate with each other. The one or more networks 142 may include any one or combination of multiple different types of networks, such as cellular networks, wireless networks, Local Area Networks (LANs), Wide Area Networks (WANs), the Internet, and so on.

Example Interfaces

Figure 2:
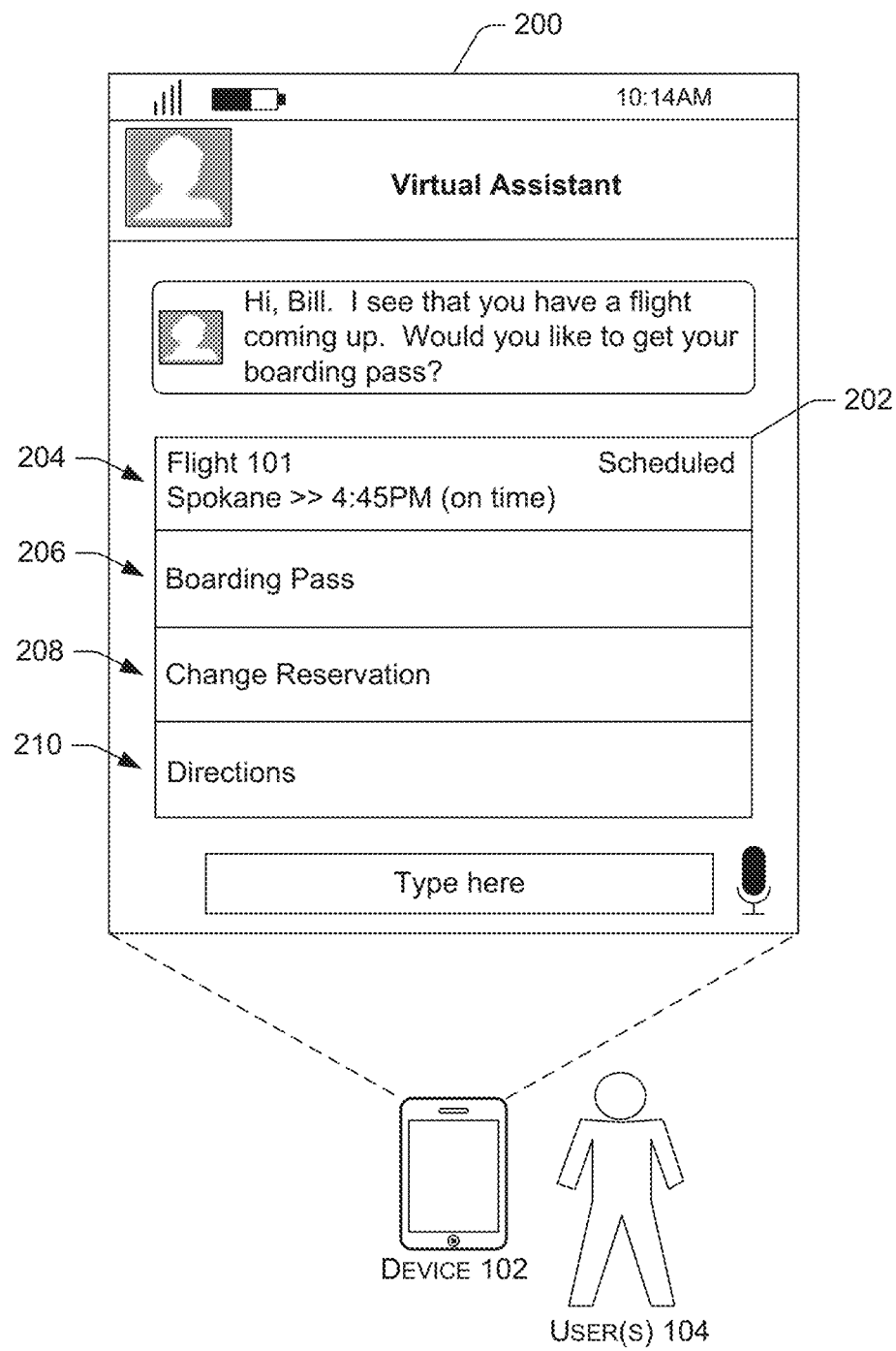
FIG. 2 illustrates an example conversation user interface that displays a conversation item for a future event associated with a user.

FIG. 2 illustrates an example conversation user interface 200 that displays a conversation item 202 for a future event associated with the user 104. Here, the virtual assistant 112 has referenced contextual information related to the user 104, namely event information identifying one or more future or past events associated with the user 104 (e.g., a calendar of the user 104, information from an airline site where the user 104 purchased a flight, or any other information source). From the contextual information, the virtual assistant 112 has identified an upcoming flight for the user 104. Further, based on other contextual information, such as a location of the user 104, environmental data (e.g., background noise), a date and time, etc., the virtual assistant 112 has determined that the user 104 may be interested in information concerning the flight. For example, if it is two hours before a scheduled flight, the virtual assistant 112 may determine that the user 104 may be interested in flight information.

Accordingly, the virtual assistant 112 may provide the conversation item 202 through the conversation user interface 200, which includes information that may be relevant to the upcoming flight (e.g., information that is relevant to a future event). The conversation item 202 may include an item 204 that provides a status of the flight (e.g., indicating a time that the flight departs and that the flight is on time). Further, the conversation item 202 may include an item 206 to obtain a board pass, an item 208 to change a reservation, and/or an item 210 to view directions to the airport. Any of the items 204-210 may be selected to provide further information and/or perform a task.

Although four items are illustrated in the example conversation item 202, any number of items may be included. Further, although the item 204 is illustrated in this example as including information that may be relevant to the user 104 (e.g., flight status information), any number of items of the conversation item 202 may include information (e.g., information for the particular content that the item represents). Additionally, or alternatively, any number of the items 204-210 may be represented with an icon or other interface element, which may or may not be selectable to provide additional information.

In some examples, the conversation item 202 may be personalized for the user 104 based on user preferences, previous interactions of the user 104 with the virtual assistant 112, and so on. For example, the flight status item 204 may be presented due to previous requests from the user 104 for flight status information, either for this flight or another flight (e.g., in a conversation with the virtual assistant 112 for a flight that the user took last month). In another example, the boarding pass item 206 may be provided based on knowledge that the user 104 typically accesses a boarding pass before arriving at the airport (e.g., through accessing an online site of the airlines). In yet another example, the directions item 210 may be presented upon determining that the user is in a car (e.g., a device of the user 104 has synced up to a car system). In some instances, by providing the conversation item 202 the virtual assistant 112 may provide a relatively small amount of information (e.g., information that is legible on a mobile device) that may be relevant to the user 104 with respect to a context of the user 104.

Although in the example of FIG. 2, the virtual assistant 112 has provided the conversation item 202 without having interacted with the user 104 (e.g., without discussing the flight with the user in a last minute), in some instances the virtual assistant 112 may provide the conversation item 202 in response to input from the user 104. For example, the item 202 may be presented in response to a request for a flight status. Here, the items 206-210 may also be included even though the user 104 has not requested such information. In another example, the item 202 is presented in response to the user 104 booking a rental car at the destination of the flight (e.g., through a conversation with the user 104).

Figure 3:
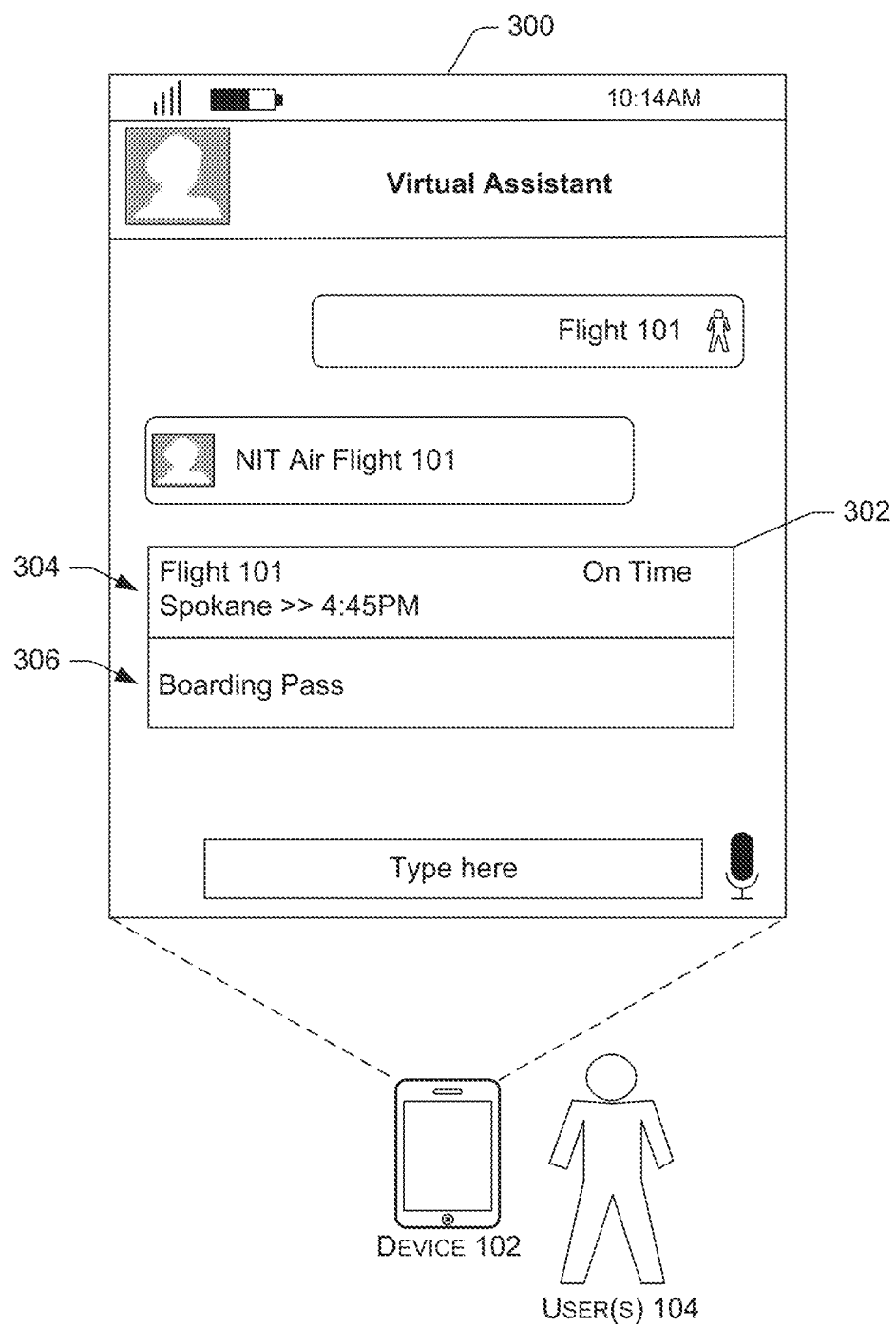
FIG. 3 illustrates an example conversation user interface that displays a conversation item for a mixed response to input that is open to multiple interpretations.

FIG. 3 illustrates an example conversation user interface 300 that displays a conversation item for a mixed response to input that is open to multiple interpretations. In this example, the user 104 has simply stated "Flight 101". This input may represent contextual information for the current conversation. Although the virtual assistant 112 may be able to identify this input as corresponding to NIT Air Flight 101 (e.g., based on a reservation of the user 104 with this flight), this input may still be relatively vague as to what the user 104 is requesting of the virtual assistant 112. That is, there may be multiple interpretations as to what information or task the virtual assistant 112 should provide or perform as a response (e.g., flight status information, check-in the user 104, change flights, obtain a boarding pass, etc.). As such, the virtual assistant 112 may provide a mixed response information item 302 that includes a first item 304 that satisfies one of the multiple interpretations of the input (e.g., flight status) and a second item 306 that satisfies another of the multiple interpretations of the input (e.g., obtain boarding pass). The items 302 and/or 304 may be selectable so that more detailed information may be provided and/or a task may be performed (e.g., obtain a boarding pass). The task may satisfy one of the multiple interpretations.

Figure 4:
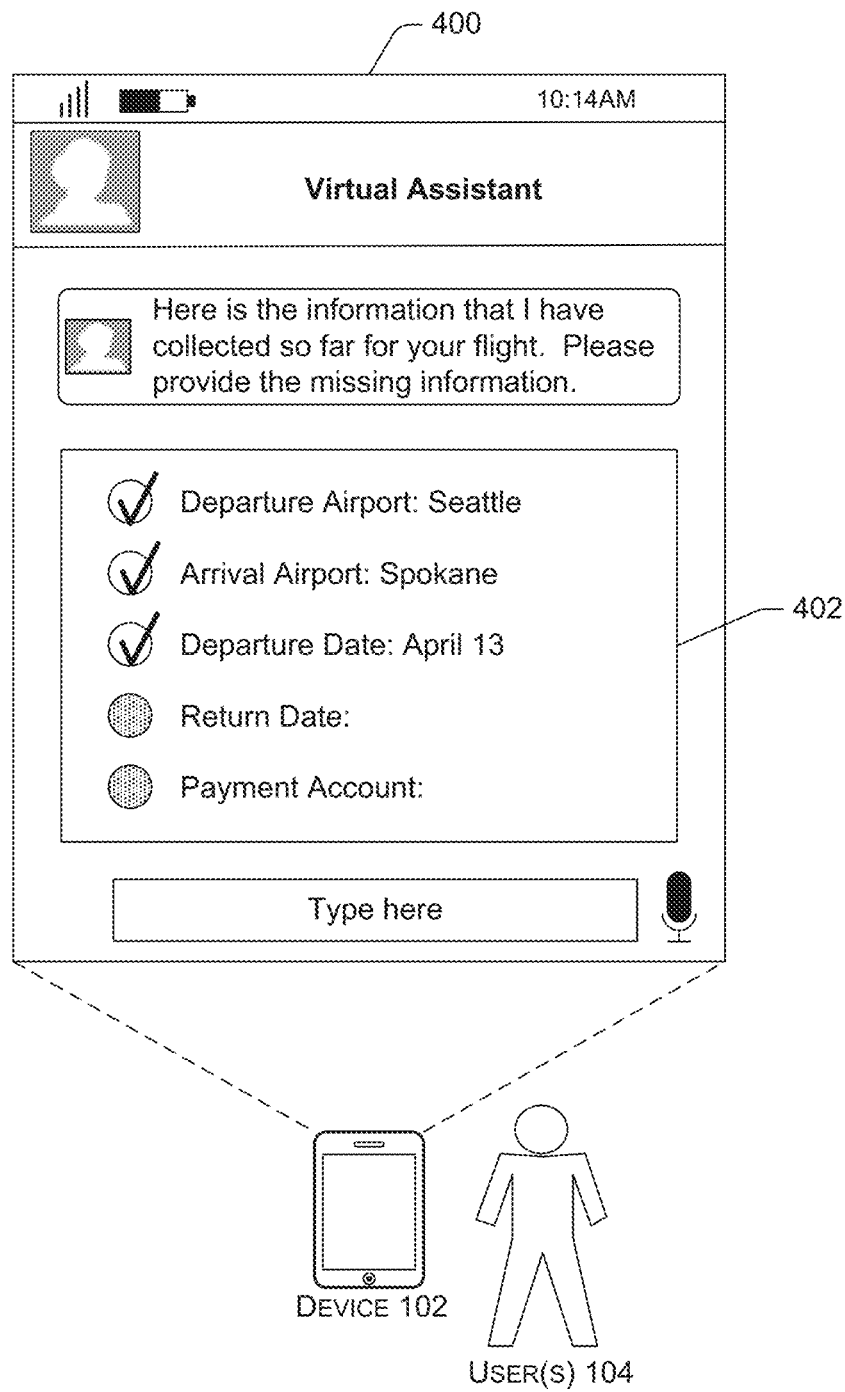
FIG. 4 illustrates an example conversation user interface that displays a conversation item for indicating what information has been obtained and what information is needed to perform a task.

FIG. 4 illustrates an example conversation user interface 400 that displays a conversation item for indicating what information has been obtained and what information is needed to perform a task. In this example, the virtual assistant 112 has obtained (e.g., collected) a portion of information that is needed for the virtual assistant 112 to reserve a flight for the user 104. This portion of information may be obtained through input of a current or previous conversation and/or through other sources, such as a user profile (e.g., indicating an age, gender, etc.), user preferences (e.g., indicating a home airport). In this example, the user 104 has interacted with the virtual assistant 112 to provide a departure airport, arrival airport, and departure date. However, in order for the virtual assistant 112 to book the requested flight, the virtual assistant 112 still needs a return date and a payment account. As such, the virtual assistant 112 may provide a missing information item 402 that indicates the portion of the information that has been obtained (e.g., departure airport, arrival airport, and departure date) and indicates a missing portion of the information that is needed for the virtual assistant 112 to perform the task (e.g., return date and payment account). The user 104 may then provide the missing portion of the information.

Although in the example user interface 400 the collected information is indicated with a check mark and the missing information is indicated with a stippling circle, any type of indicators may be provided (e.g., different colors, plus and minus, etc.). By providing the missing information item 402 within the user interface 400, the user 104 may easily determine what information has been obtained and what information is missing. This may enable the user 104 to input the missing information without inputting information that has already been obtained.

Figure 5:
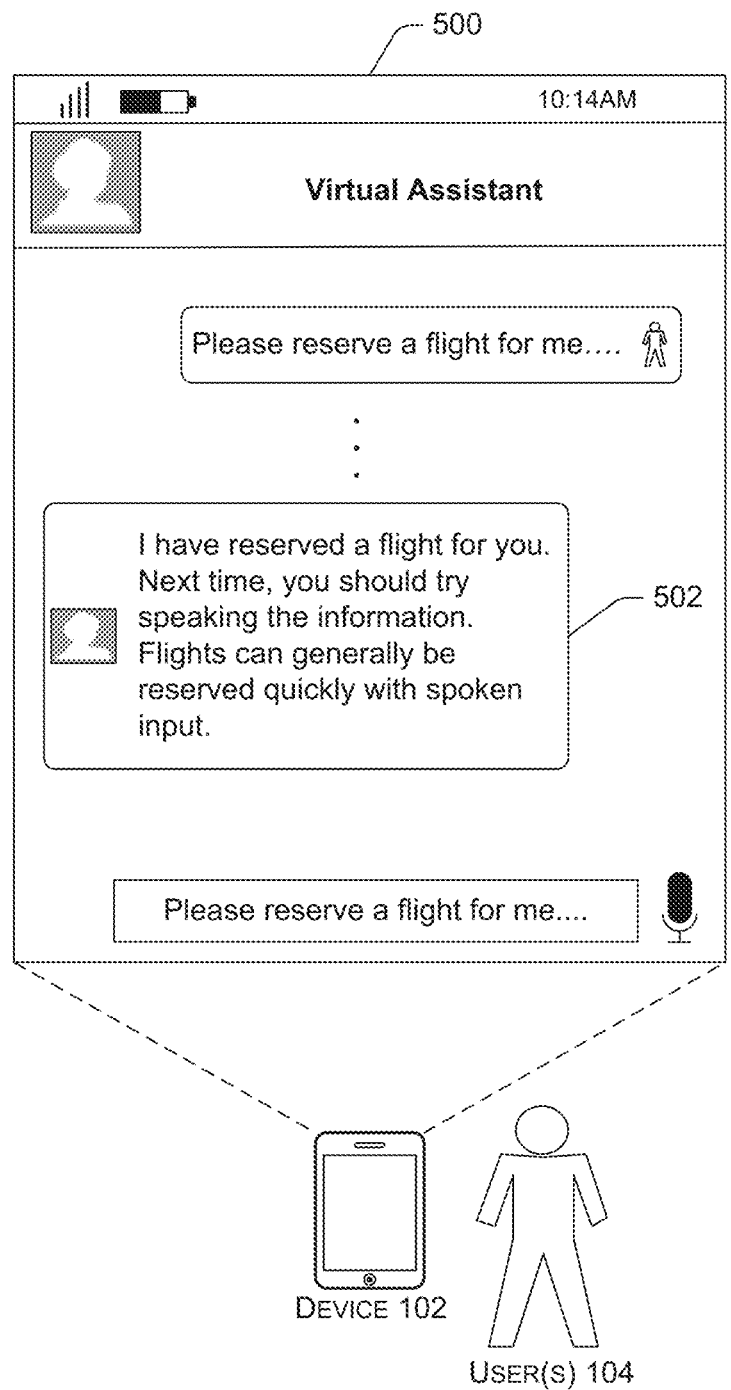
FIG. 5 illustrates an example conversation user interface that displays a conversation item for suggesting an alternative input mode to an input mode that is currently used by a user.

FIG. 5 illustrates an example conversation user interface 500 that displays a conversation item for suggesting an alternative input mode to an input mode that is currently used by the user 104. In this example, the user 104 may have interacted with the virtual assistant 112 through a particular type of input mode to reserve a flight, namely text input. Here, the text input may require a relatively large amount of text (e.g., multiple lines) to provide the necessary information, which may consume a substantial amount of time for the user 104. Accordingly, upon reserving the flight for the user 104 or at any other time (e.g., while the user 104 provides the necessary information), the virtual assistant 112 may provide a suggestion item 502 that suggests an alternative input mode to the input mode that is currently used by the user 104.

The alternatively input mode may enable an enhanced interaction of the user 104 with the virtual assistant 112, in comparison to the input mode that is currently used by the user 102. For example, the alternative input mode may enable the user 104 to input information for a request more quickly, in comparison to the currently used input mode. Further, the alternative input mode may enable information to be received more accurately. In one example, the virtual assistant 112 may suggest that the user 104 use text input to identify an individual that has a name that is difficult to pronounce. In the example of FIG. 5, the virtual assistant 112 may suggest that the user 104 use speech next time when reserving a flight.

In some instances, the virtual assistant 112 may provide the suggestion item 502 when the user 104 has used a particular input mode over an extended period of time and/or when the user 104 has used the particular input mode more than a particular number of times. For example, the suggestion item 502 may be provided when the user 104 has used text the last three times to reserve a flight.

Although the example of FIG. 5 illustrates techniques for suggesting an alternative input mode, the techniques may alternatively, or additionally, suggest any type of interface functionality. In one example, the virtual assistant 112 may be unable to understand input that is provided by the user 104, which may cause the user 104 to repeat the same input over and over. Here, the virtual assistant 112 may identify that the user 104 is repeating the same input and may suggest that the user 104 utilize speech correction functionality (e.g., a correction interface) to correct the input and/or to teach the virtual assistant 112 what is being input. In another example, the virtual assistant 112 may identify that the user 104 frequently (e.g., more than a threshold number of times) returns to a particular conversation item in a conversation by using a manual scroll (e.g., utilizes a scroll bar, upward swipe, or other input). Here, the virtual assistant 112 may suggest that the user 104 tag the conversation item (e.g., save the conversation item to a tray, associate the conversation item with a marking, etc.) so that the conversation item may be accessed more efficiently. In yet another example, the virtual assistant 112 may identify that the user 104 has asked the same question a particular number of times (e.g., in every conversation) and may suggest that the user 104 tag an answer provided by the virtual assistant 112 to this question (e.g., save the answer to a tray) so that the user 104 may not have to ask the same question over and over. In other examples, the virtual assistant 112 may suggest other types of interface functionality.

Figure 6:
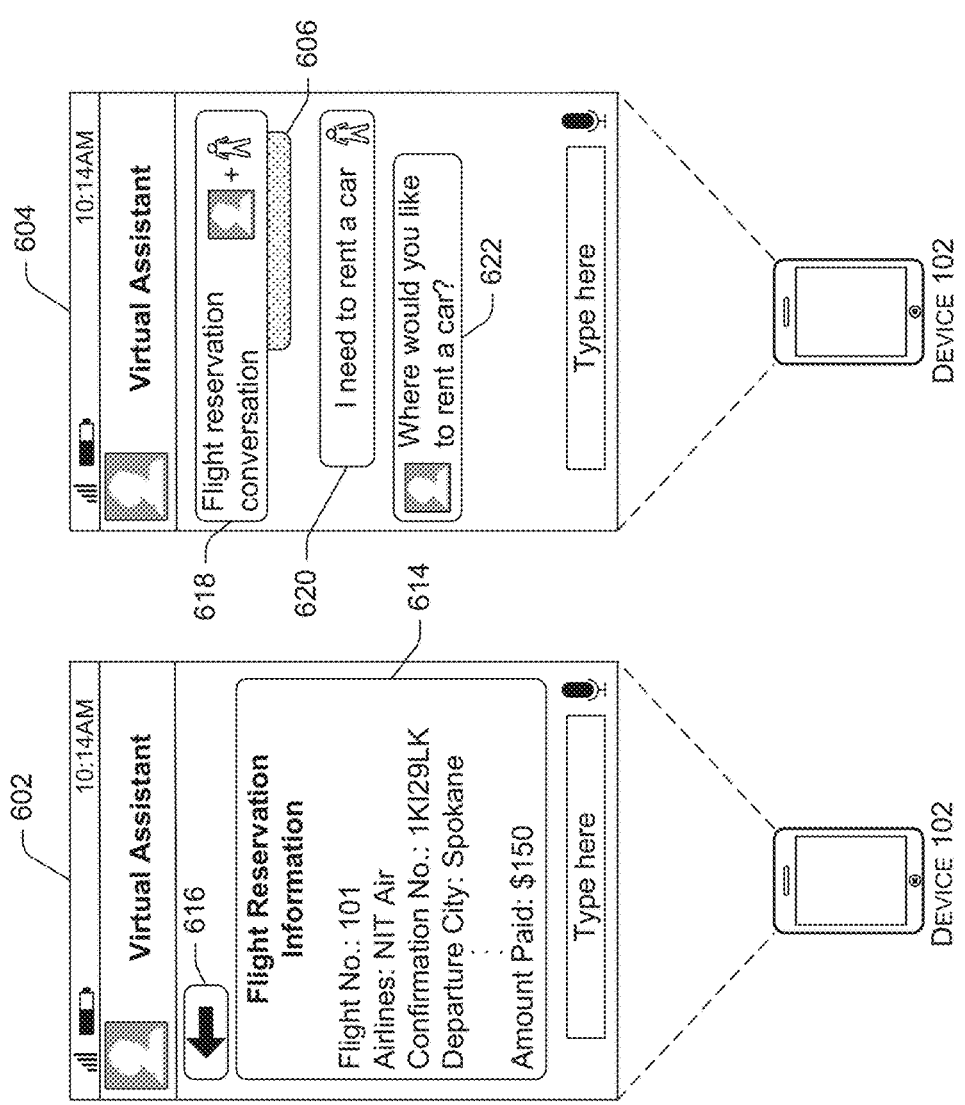
FIGS. 6A-6C illustrate example conversation user interfaces to display different levels of detail of a conversation.

FIGS. 6A-6C illustrate example conversation user interfaces 600-604 to display different levels of detail of a conversation. In particular, FIG. 6A illustrates the example conversation user interface 600 that includes an information item 606 that represents information that has been collected during a current conversation between the user 104 and the virtual assistant 112. In this example, the user 104 and the virtual assistant 112 have interacted for a number of minutes through various responses and pieces of input to reserve a flight, as illustrated in FIG. 6A by dialog representations 608-612. During this conversation the virtual assistant 112 has collected information to reserve the flight (e.g., a flight number, airlines, departure city, departure date, etc.) and, thereafter, reserved the flight. Upon reserving the flight, the virtual assistant 112 may provide the information item 606 to represent the finality of the reservation. That is, the information item 606 may represent the collected information and/or information for the task of reserving the flight in a condensed format (e.g., as an icon).

Upon selection of the information item 606, the conversation user interface 602 may be presented to the user 104, as illustrated in FIG. 6B. The conversation user interface 602 may include a conversation item 614 that presents further details for the flight reservation, such as a flight number, an airline, a confirmation number, a departure city, an amount paid, and so on. The interface 602 may also include a back button 616 to return to the conversation user interface 600. This may enable the user 104 to control the level of detail of the flight reservation information.

In some instances, when a conversation is finished, the virtual assistant 112 may provide a conversation item 618 representing a history of the conversation, as illustrated in FIG. 6C. In this example, the conversation item 618 represents a history of the flight reservation conversation in a condensed format (e.g., with an icon). The user 104 may select the conversation item 618 and return to the conversation history as illustrated in FIG. 6A. In some examples, the information item 606 that represents the flight reservation information may be at least partly hidden behind the conversation item 618, as also illustrated in FIG. 6C. That is, the conversation item 618 may be displayed in an overlaid manner over at least a portion of the information item 606. Here, the conversation item 606 may be selected to reveal the flight reservation information, as illustrated in FIG. 6B.

The conversation items 606 and/or 618 may be presented in a condensed format, as illustrated in FIG. 6C, when the virtual assistant 112 determines that the conversation for that topic has ended and/or when the user 104 so specifies (e.g., selection of an icon, swipe in an upward direction, etc.). For example, the virtual assistant 112 may determine that the flight reservation conversation has ended when the user 104 and the virtual assistant 112 begin discussing another topic (e.g., car rental), as illustrated by conversation items 620 and 622 in FIG. 6C. By providing the conversation items 606 and/or 618 in a condensed format, the conversation user interface 604 may efficiently use space of the interface 604 and/or provide a means for the user 104 to return to a previous conversation.

Figure 7:
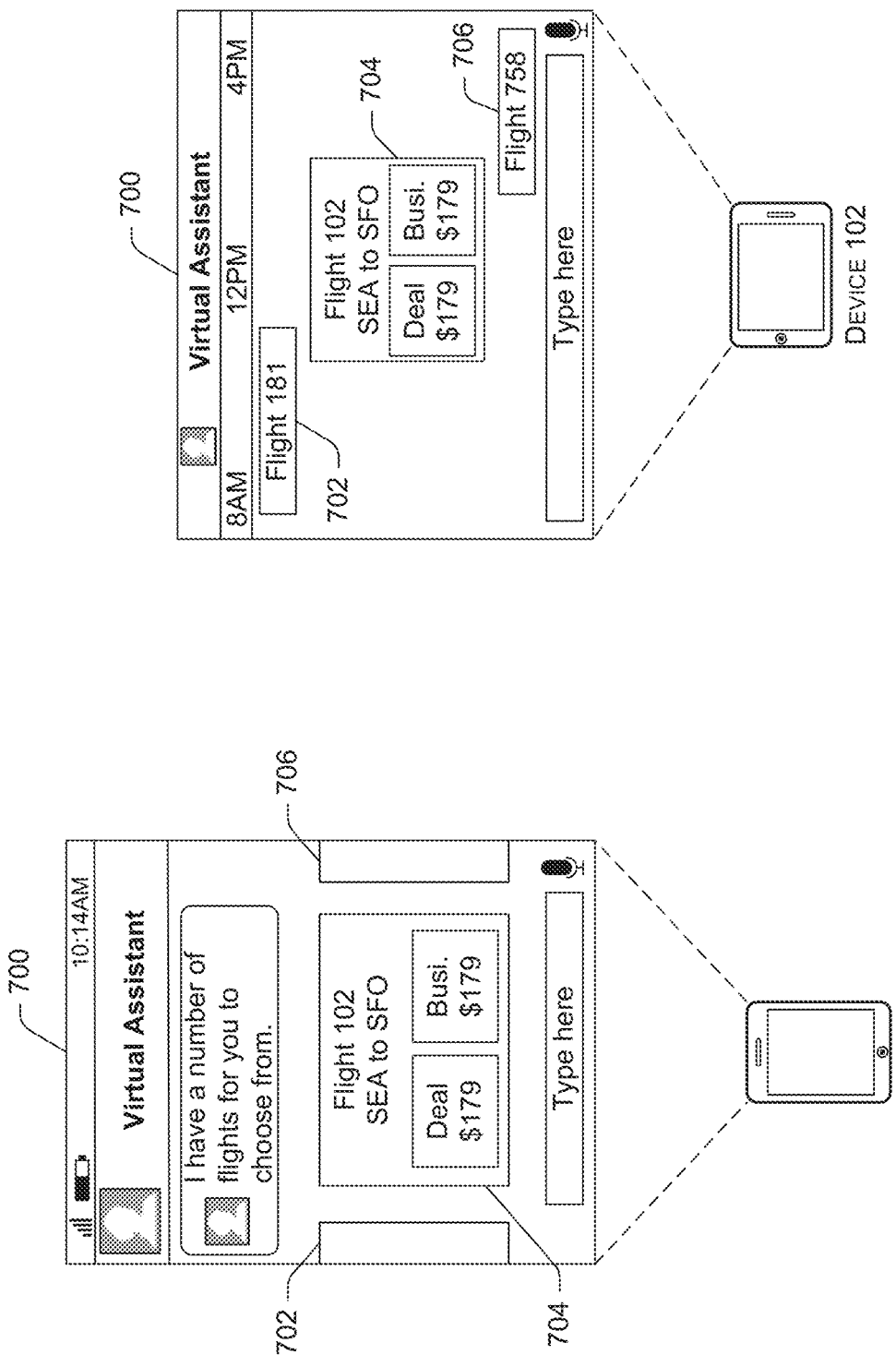
FIGS. 7A-7B illustrate an example conversation user interface to display conversation items based on an orientation of a smart device.

FIGS. 7A-7B illustrate an example conversation user interface 700 to display conversation items based on an orientation of the smart device 102. In the interface 700, the virtual assistant 112 may identify an orientation of the smart device 102 (e.g., portrait or landscape) and provide different information, or the same information, in a particular format that is adapted to the identified orientation.

In particular, FIG. 7A illustrates the conversation user interface 700 when the smart device 102 is positioned in a portrait orientation. Here, the conversation user interface 700 includes conversation items 702-706 that are scrollable in a horizontal direction (e.g., from side-to-side). The conversation items 702-706 may represent option items provided by the virtual assistant 112 for the user 104 to select (e.g., items that represent different options). In this example, the user 104 has request flight information for flights from Seattle to San Francisco and the virtual assistant 112 has provided the conversation items 702-706 as option items. Although not illustrated in FIG. 7A, the conversation items 702 and 706 may include similar information as that provided for the conversation item 704 (e.g., flight information).

FIG. 7B illustrates the conversation user interface 700 when the smart device 102 is positioned in a landscape orientation. Here, the conversation item 704 may be presented on a timeline with other flights. In this example, the conversation item 704 is positioned to indicate the flight time (e.g., that the flight departs around 11 AM and arrives around 2 PM). The conversation user interface 700 also includes the conversation items 702 and 706 at times when those flights are scheduled. Upon selection of one of the conversation items 702 or 706, the conversation item may be displayed in a similar manner as that of the conversation item 704.

Figure 8:
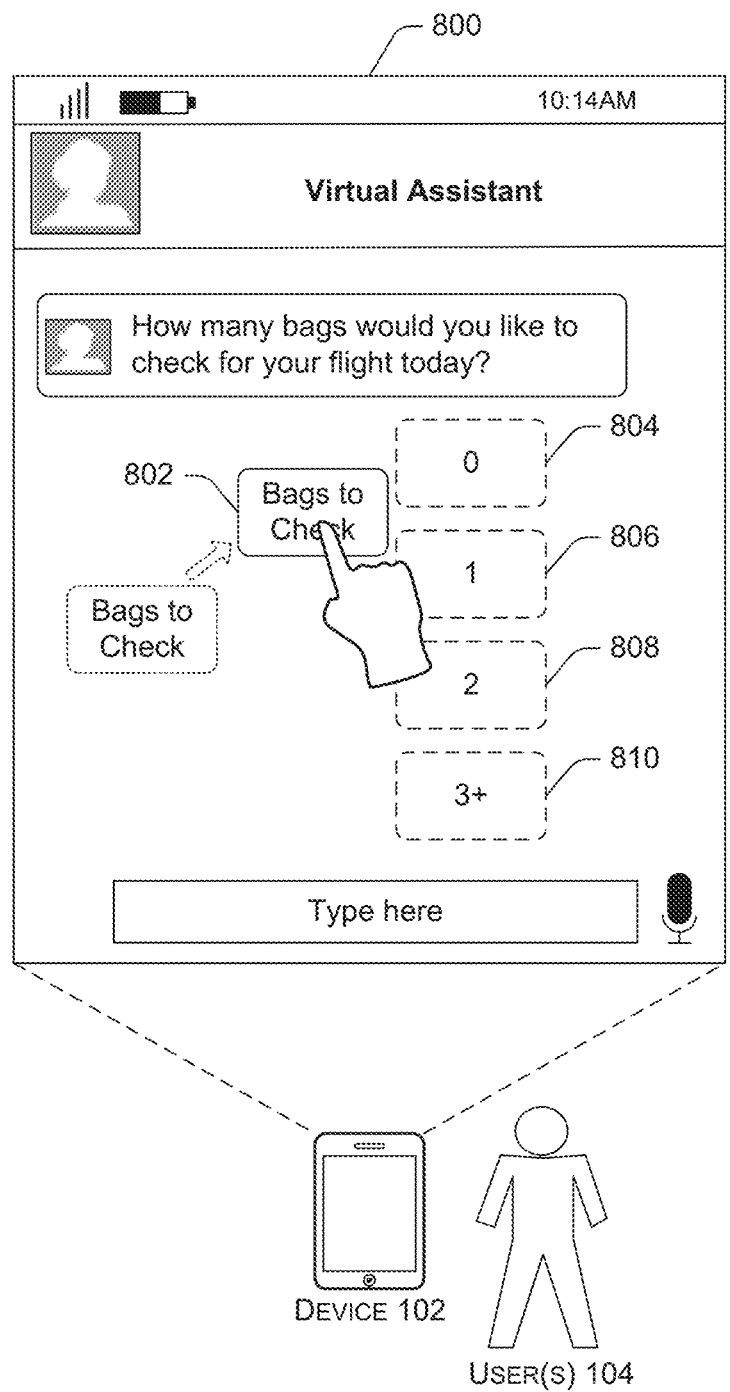
FIG. 8 illustrates an example conversation user interface for receiving input from a user through dragging a conversation item onto another conversation item.

FIG. 8 illustrates an example conversation user interface 800 for receiving input from the user 104 through dragging a conversation item onto another conversation item. In this example, the virtual assistant 112 is requesting information to perform a task (e.g., check-in bags for the user 104). To obtain the information, the virtual assistant 112 presents an inquiry for the user 104 to respond to, namely "How many bags would you like to check for you flight today?" The inquiry is based on a conversation with the user 104. The inquiry is represented by presenting conversation items 802-810 such that the item 802 is movable and the items 804-810 receive the item 802. The user 104 may answer the inquiry by moving the item 802 onto (e.g., on top of) or in contact with one of the items 804-810. In this example, the user 104 has selected the item 802 at an initial position and is dragging the item 802 onto the item 804 to indicate that the user 104 will be checking "0" bags onto the flight. In response to receiving such input from the user 104, the virtual assistant 112 may perform the requested task (e.g., check-in "0" bags). Although the example conversation interface 800 illustrates five conversation items (e.g., conversation items 802-810) to answer an inquiry, any number of conversation items may be used.

Although the example of FIG. 8 receives an answer to an inquiry through moving a conversation item to another conversation item, in some instances the answer may be provided through a simultaneously selection (e.g., touch) of two or more conversation items (e.g., multi-touch) and/or through selecting conversation items in a particular order.

Figure 9:
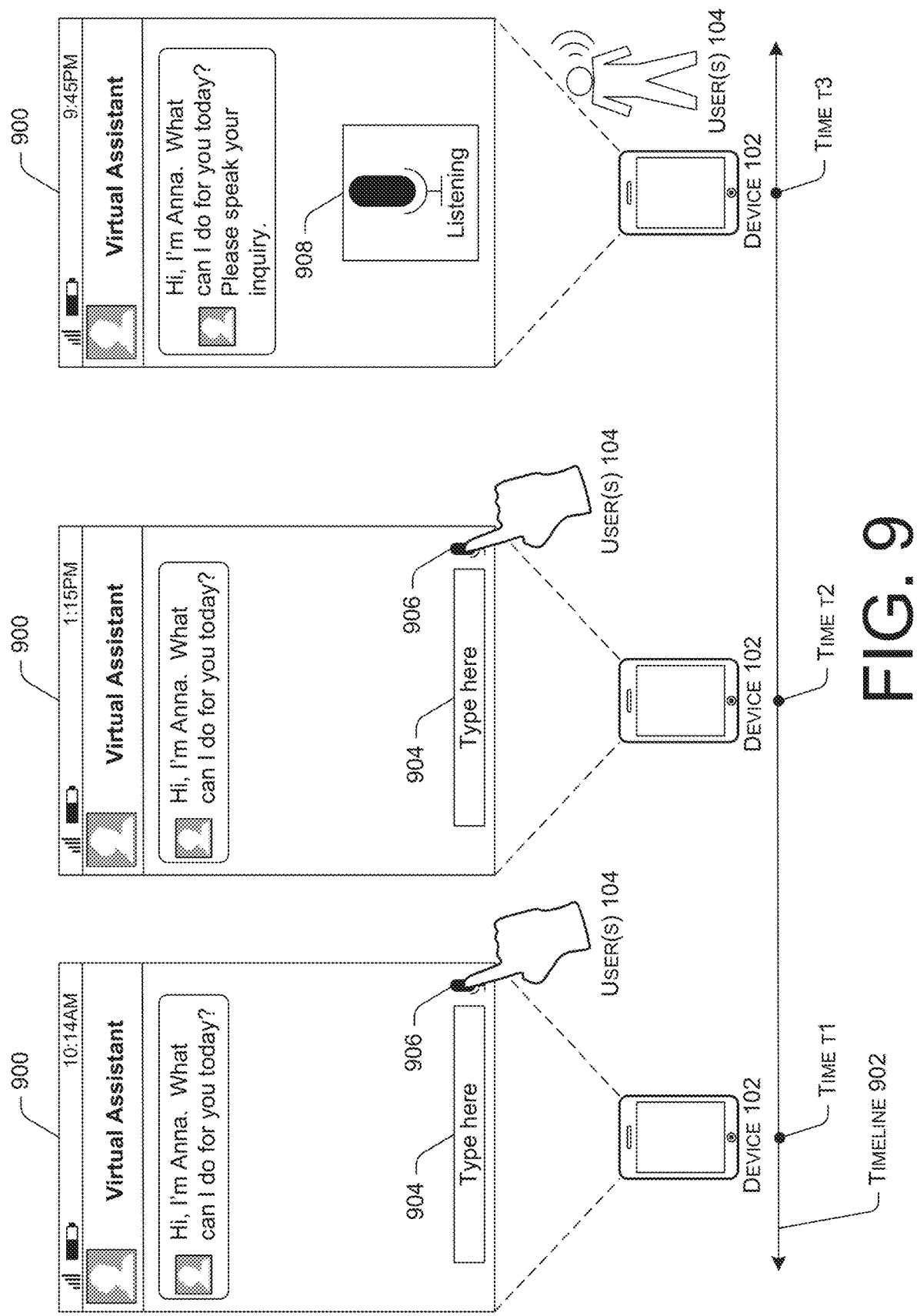
FIG. 9 illustrates an example conversation user interface that controls an input mode based on contextual information.

FIG. 9 illustrates an example conversation user interface 900 that controls an input mode based on contextual information. In this example, the conversation user interface 900 is illustrated as adapting over time based on input from the user 104, as illustrated by the change in the interface 900 over a timeline 902. In particular, at time t1, the conversation user interface 900 is presented with a text input field 904 and a microphone icon 906 to enable the user 104 to input text and/or input speech. Upon selection of the text input field 904, a touch screen keyboard may be displayed within the conversation user interface 900. Meanwhile, selection of the microphone icon 906 may enable a microphone of the smart device 102 (e.g., begin recording audio). In this example, at time t1, the user 104 selects the microphone icon 906 to input information through speech.

At time t2, the conversation user interface 900 is presented again with the text input field 904 and the microphone icon 906 enabled to receive text and/or speech input. Here, the user 104 also selects the microphone icon 906 to provide speech input. In some instances, the input modes used at time t2 and/or the input mode used at time t1 may be saved to a profile of the user 104 for future reference.

At time t3, the virtual assistant 112 references the previous input modes that were used at times t1 and t2 to determine that the user 104 prefers to use speech input. Accordingly, at time t3, the conversation user interface 900 is presented (e.g., initialized) with the microphone of the smart device 102 enabled to receive audio. That is, an input mode of the conversation user interface 900 may be controlled so that a speech input mode is configured as a primary mode of input (e.g., the microphone is enabled and/or the text input field 904 and/or microphone icon 906 are hidden). As illustrated at time t3, the interface 900 may present an icon 908 to indicate that the smart device 102 is listening for speech input. As such, the conversation user interface 900 may adapt the input mode of the interface 900 based on one or more pieces of contextual information, in this example, input history indicating one or more input modes that the user 104 has previously used to interact with the conversation user interface 900.

Although the example of FIG. 9 updates the input mode of the conversation user interface 900 based on input received at two different instances, the input mode may be updated based on any number of previous input instances (e.g., when any threshold is met). In one example, the conversation user interface 900 may be controlled to enable whichever input mode was used during a last conversation.

Further, although the example conversation user interface 900 adapts the input mode based on input mode history of the user 104, in other examples the input mode may adapt based on other information. In one example, the input mode is adapted to the most suitable input mode for a location of the user 104. For instance, when the user 104 is determined to be in a meeting (e.g., based on calendar information), the conversation user interface 900 may select a text input mode to be utilized and display a keyboard so that the user 104 may utilize text input. In another example, when the user 104 is located in a car (e.g., based on a connection of the smart device 102 to a car system), the conversation user interface 900 may enable the microphone to receive speech input. That is, the microphone may be turned-on and listen for audio (e.g., begin recording).

In another example, the input mode of the conversation user interface 900 is adapted based on a type of information that the virtual assistant 112 and/or the user 104 may be providing (e.g., a type of conversation). To illustrate, if the virtual assistant 112 is requesting an account number or password from the user 104, the virtual assistant 112 may display a keyboard in order to provide the information in a more secured manner. In some instances, the virtual assistant 112 may transition to the keyboard to receive the account number or password and then transition back to a previous input mode. In a further example, the virtual assistant 112 may learn that the user 104 prefers to utilize the keyboard for an account number or password, due to user input that enables the keyboard when such information is requested by the virtual assistant 112.

Alternatively, or additionally, in some instances the conversation user interface 900 may utilize selectable touch icons to receive touch input instead of utilizing the text input filed 904 and/or the microphone icon 906. For example, if the virtual assistant 112 determines that the user 104 prefers touch input (e.g., based on the user 104 selecting icons in previous conversations), the conversation user interface 900 may be presented with selectable icons. This may replace the text input filed 904 and/or the microphone icon 906.

Figure 10:
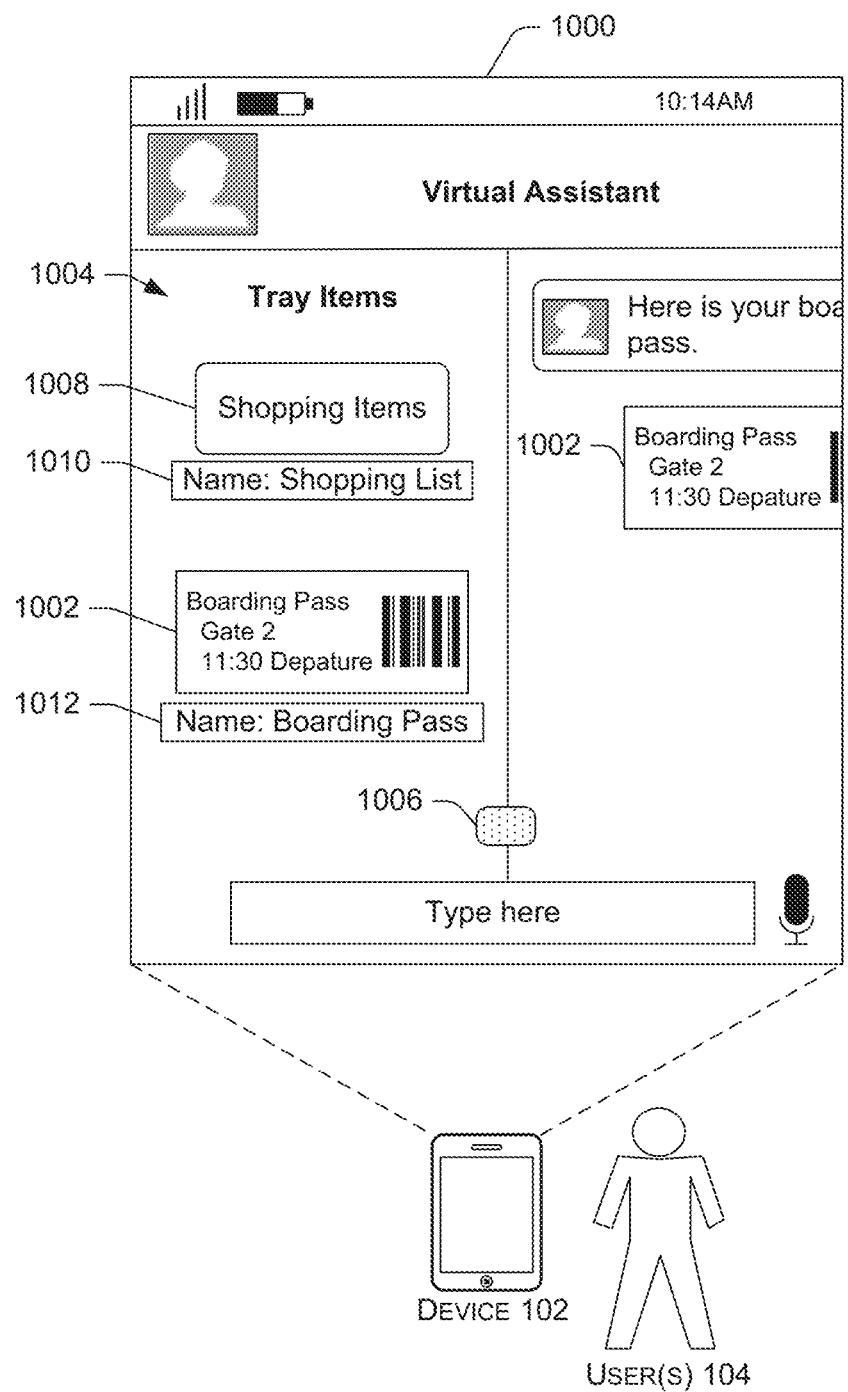
FIG. 10 illustrates an example conversation user interface that tags a conversation item by saving the conversation item to a tray.
Figure 11:
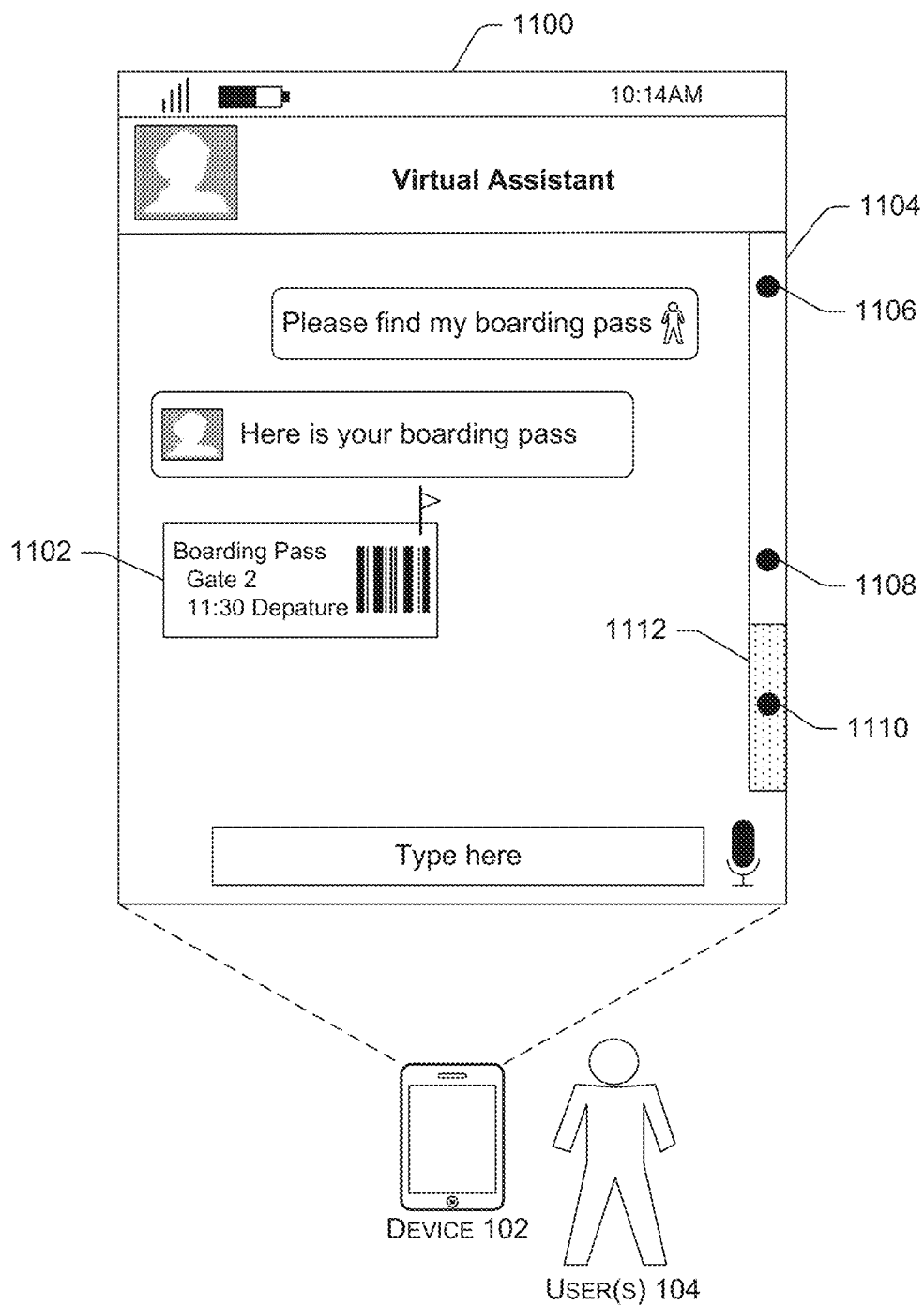
FIG. 11 illustrates an example conversation user interface that tags a conversation item by associating the conversation item with an indicator.

FIGS. 10 and 11 illustrate example conversation user interfaces 1000 and 1100 to tag a conversation item. In FIG. 10, a conversation item may be tagged by saving the conversation item to a tray that is associated with the conversation user interface 1000. In particular, as illustrated in FIG. 10, the virtual assistant 112 has provided a conversation item 1002, namely a boarding pass, as part of a conversation with the user 104. Thereafter, the user 104 accessed a tray 1004 for saving conversation items. The tray 1004 may be accessed by particular user input (e.g., swiping to the side) and/or by selecting an icon 1006. In this example, the user 104 has selected the conversation item 1002 and dragged the item 1002 into the tray 1004 to be saved. As illustrated, the tray 1004 also includes a conversation item 1008 related to shopping items. In some instances, conversation items that are saved to the tray 1004 may be removed from the conversation, while in other instances the tray 1004 saves copies of the conversation items. By saving conversation items to the tray 1004, the user 104 may efficiently access conversation items that may have particular relevance to the user 104.

In some instances, the tray 1004 may enable the user 104 to provide identifying information for a conversation item that is saved. For example, the tray 1004 may include a field 1010 to name the conversation item 1008 (e.g., shopping list) and/or a field 1012 to name the conversation item 1002 (e.g., boarding pass). Although the fields 1010 and 1012 are illustrated as being separate from the conversation items 1002 and 1008, the fields 1010 and 1012 may be part of the items 1002 and 1008 such that selection of an item may enable the user 104 to provide a name. After a conversation item has been named, the user 104 and/or the virtual assistant 112 may refer to the conversation item by its name.

Although the example of FIG. 10 discusses the user 104 moving items to the tray 1004, in some instances the virtual assistant 112 may perform such actions. For example, upon completion of a conversation and providing a conversation item that represents the finality of the conversation, the virtual assistant 112 may save the conversation item to the tray 1004.

In FIG. 11, a conversation item may be tagged by associating the conversation item with an indicator. In particular, FIG. 11 illustrates a conversation item 1102 that is tagged with a flag indicator that visually indicates that the conversation item is tagged. Although a flag is used, other indicators may alternatively, or additionally, be used, such as displaying the conversation item 1102 with a different color, providing an icon next to the conversation item 1102, and so on.

Although not illustrated in FIG. 11, in some instances a conversation item that is tagged with an indicator may be associated with identifying information. For example, a conversation item may be named with a field, such as the fields 1010 and 1012 of FIG. 10. As noted above, this may enable the conversation item to be easily referred to in a conversation.

As illustrated in FIG. 11, the conversation user interface 1100 may include a timeline bar 1104 that indicates a location of the conversation over time. The timeline bar 1104 may display markings 1106-1110 to indicate locations of conversation items that have been tagged, either through associating the conversation items with flags or storing the conversation items to a tray. For example, the marking 1110 may correspond to the conversation item 1102 which is tagged. The timeline bar 1104 may also include a section 1112 to indicate a current location of the conversation (e.g., the currently displayed information in the conversation user interface 1100). When the user 104 desires to view a tagged conversation item, the user 104 may select one of the markings 1106-1100 and the conversation user interface 1100 may navigate to the location in the conversation where the conversation item is located.

Although FIGS. 10 and 11 generally depict separate tagging techniques, it should be appreciated that these tagging techniques may be used in combination. For example, if a conversation item is tagged through associating the item with a flag, as shown in FIG. 11, the conversation item may be automatically stored to a tray, as shown in FIG. 10.

Example Processes

FIGS. 12-17 illustrate example processes 1200-1700 for employing the techniques described herein. For ease of illustration processes 1200-1700 are described as being performed in the architecture 100 of FIG. 1. For example, one or more of the individual operations of the processes 1200-1700 may be performed by the smart device 102 and/or the virtual assistant service 116. In many instances, the processes 1200-1700 are performed by the virtual assistant 112 implemented at least in part on the smart device 102. However, the processes 1200-1700 may be performed in other architectures. Moreover, the architecture 100 may be used to perform other processes.

The processes 1200-1700 (as well as each process described herein) are illustrated as a logical flow graph, each operation of which represents a sequence of operations that can be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order and/or in parallel to implement the process. Further, any number of the described operations may be omitted.

Figure 12:
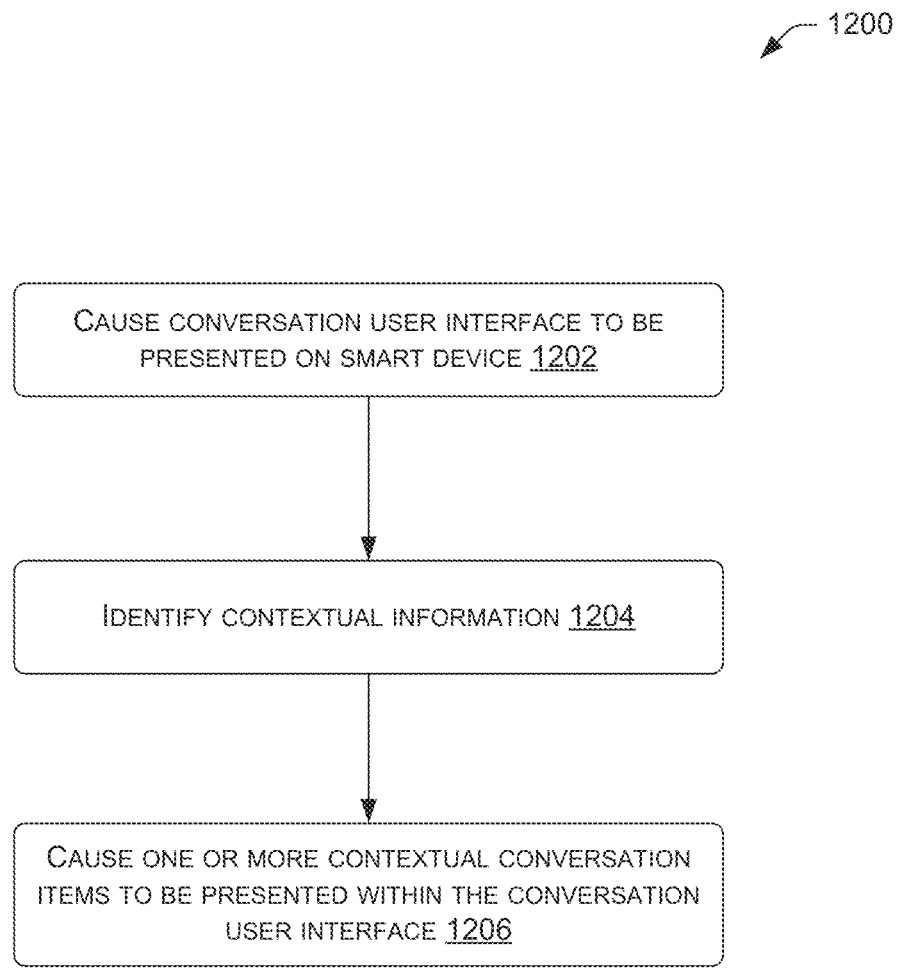
FIG. 12 illustrates an example process for identifying contextual information related to a conversation between a user and a virtual assistant and presenting a contextual conversation item(s) based on the contextual information.

FIG. 12 illustrates the example process 1200 for identifying contextual information related to a conversation between a user and a virtual assistant and presenting a contextual conversation item(s) based on the contextual information.

At 1202, the smart device 102 may cause a conversation user interface to be presented on the smart device 102. The conversation user interface may enable a conversation between a user of the smart device 102 and a virtual assistant implemented at least in part on the smart device 102.

At 1204, the smart device 104 may identify (e.g., determine) contextual information that is related to the conversation. The contextual information may comprise, for example, a location of a user, event information related to a past or future event associated with the user, environmental data obtained by a sensor of the smart device 102, a preference of the user, conversation history of the user with the virtual assistant in a current conversation, conversation history of the user with virtual assistant in a previous conversation, information that is needed for the virtual assistant to perform a task, an input mode that is currently or was previously used by the user to interact with the virtual assistant, information that is collected during a current conversation between the user and the virtual assistant, information that identifies an orientation of the smart device 102, and so on. In some instances, the smart device 104 operates in cooperation with the virtual assistant service 116 to identify the contextual information. For example, the virtual assistant service 116 may identify the contextual information and send a message to the smart device 102 that includes the information and/or identifies the information.

At 1206, the smart device 102 may cause one or more contextual conversation items to be presented within the conversation user interface based at least in part on the contextual information. The one or more contextual conversation items may comprise, for example, an information item that provides information that is relevant to a future event associated with the user, a mixed response information item that includes a first item that satisfies one of multiple interpretations of input of the user and a second item that satisfies another of the multiple interpretations of the input of the user, a missing information item that indicates a portion of information that has been obtained by the virtual assistant to perform a task and indicates a missing portion of the information that is needed for the virtual assistant to perform the task, a suggestion item that suggests an alternative input mode to an input mode that is currently used by the user, an information item that represents information that is collected by the virtual assistant during the conversation between the user and the virtual assistant, a conversation item that is tagged by the user, an input mode item for receiving input from the user according to an inferred mode of input of the user (e.g., preferred input mode), and so on.

Figure 13:
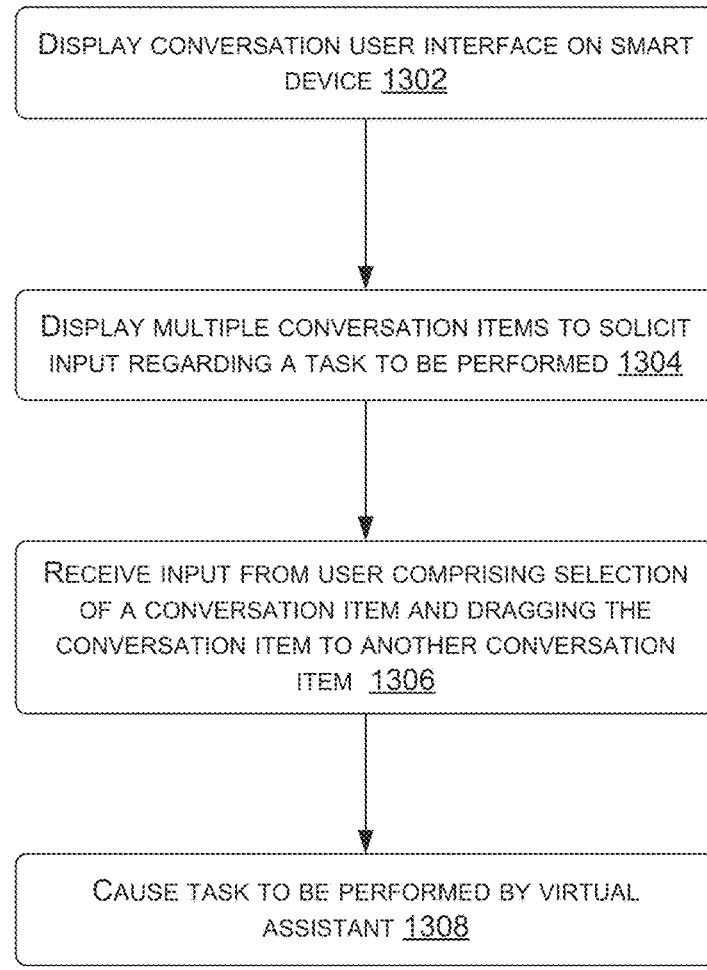
FIG. 13 illustrates an example process for performing a task based on input from a user through a conversation user interface that includes a selection of a conversation item and dragging the conversation item to another conversation item.

FIG. 13 illustrates the example process 1300 for performing a task based on input from a user through a conversation user interface of a virtual assistant that includes a selection of a conversation item and dragging the conversation item to another conversation item.

At 1302, the smart device 102 may display a conversation user interface on the smart device 102 to enable a conversation between a user of the smart device 102 and a virtual assistant implemented at least in part on the smart device 102.

At 1304, the smart device 102 may display multiple conversation items within the conversation user interface to solicit input from the user regarding a task to be performed by the virtual assistant. The multiple conversation items may represent an inquiry of the virtual assistant that is based at least in part on the conversation between the user and the virtual assistant.

At 1306, the smart device 102 may receive input from the user that selects a conversation item of the multiple conversation items and drags the selected conversation item to another conversation item of the multiple conversation items. For example, the user may drag the conversation item on top of the other conversation item. This may indicate an answer to the inquiry of the virtual assistant.

At 1308, the smart device 102 may cause the task to be performed by the virtual assistant. The task may be performed based at least in part on the input that is received from the user (e.g., the answer to the inquiry).

Figure 14:
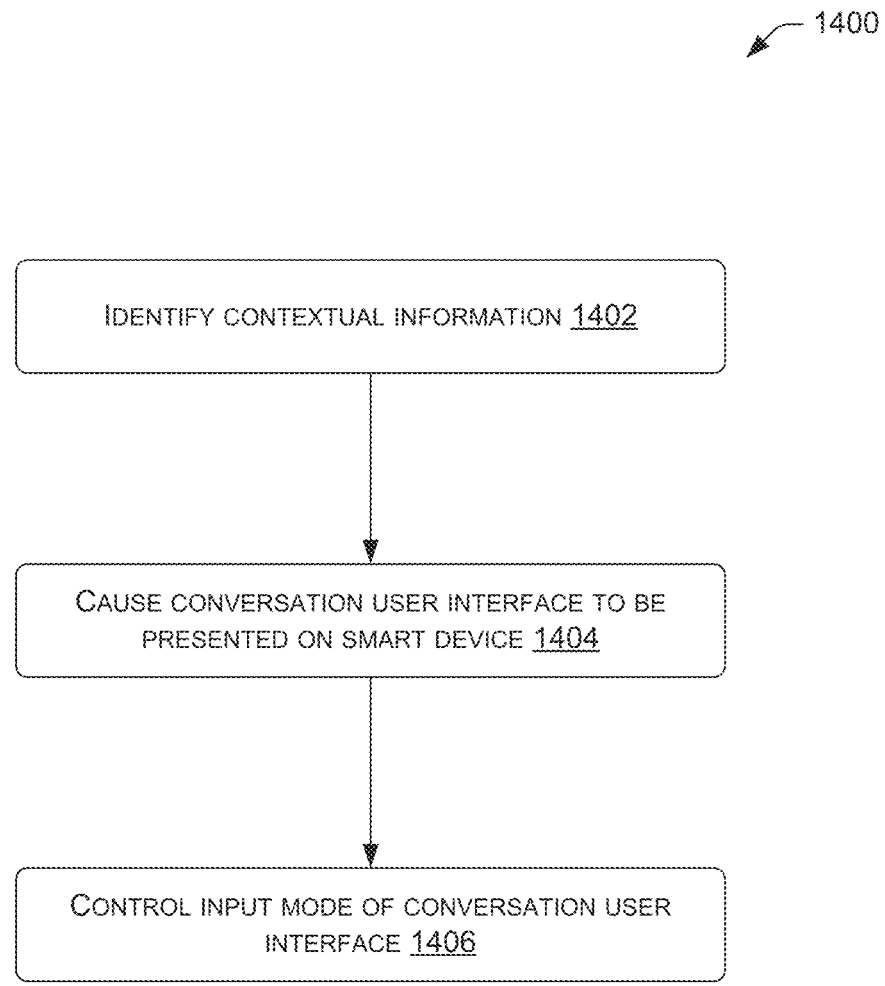
FIG. 14 illustrates an example process for controlling an input mode of a conversation user interface based on contextual information associated with a user.

FIG. 14 illustrates the example process 1400 for controlling an input mode of a conversation user interface based on contextual information associated with a user.

At 1402, the smart device 102 may identify contextual information associated with a user. The contextual information may comprise, for example, location information indicating a location of the user, input history indicating one or more input modes that the user has previously used to interact with the conversation user interface or another user interface, information indicating an inferred (e.g., preferred) type of input mode of the user (e.g., in a user profile), or any other type of information.

At 1404, the smart device 102 may cause a conversation user interface to be presented on the smart device 102 to enable a conversation between the user of the smart device 102 and a virtual assistant implemented at least in part on the smart device 102.

At 1406, the smart device 102 may control an input mode of the conversation user interface according the contextual information. The conversation user interface may be configured with the input mode as a primary mode of input. For example, the smart device 102 may control the interface to be presented with an input mode that is selected based on a location of the smart device 102 (e.g., select an input mode from among input modes that are available to the smart device 102). In another example, the smart device 102 may control the interface such that the conversation user interface is presented with an input mode from among one or more input modes that have been previously used by the user (e.g., interface is configured with a preferred type of input mode of a user). Here, the smart device 102 may infer which type of input mode is preferred by the user. If, for example, an inferred type of input mode is text input, the interface may display a keyboard when initialized (e.g., within the conversation user interface or proximate to the interface). If the inferred type of input mode is touch input, the interface may display selectable icons to receive touch input when the interface is initialized. Further, if the inferred type of input mode is speech input, the interface may enable (e.g., power-on) a microphone of the smart device 102 when the interface is initialized and begin listening for audio.

Figure 15:
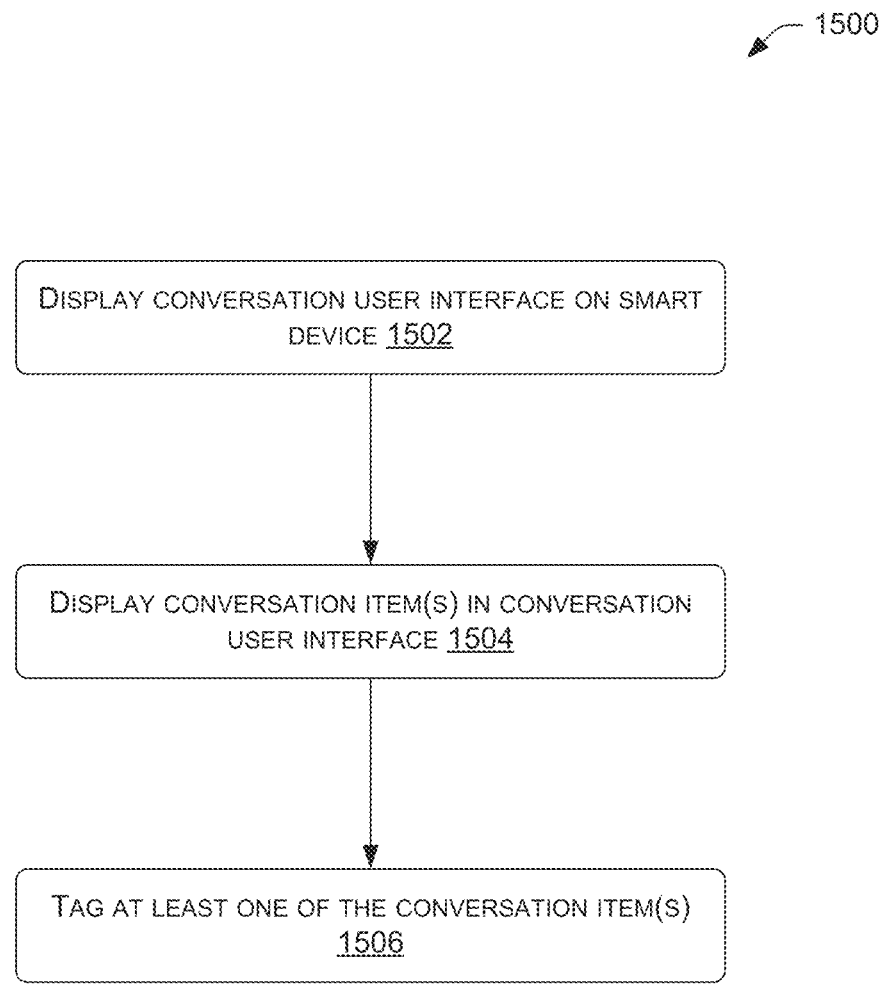
FIG. 15 illustrates an example process for tagging conversation items of a conversation user interface.

FIG. 15 illustrates the example process 1500 for tagging conversation items of a conversation user interface.

At 1502, the smart device 102 may display a conversation user interface on the smart device 102 to enable a conversation between a user of the smart device 102 and a virtual assistant implemented at least in part on the smart device 102.

At 1504, the smart device 102 may display one or more conversation items in the conversation user interface. Each of the one or more conversation items may represent input of the user, a response of the virtual assistant, or both.

At 1506, the smart device 102 may tag at least one conversation item of the one or more conversation items. For example, the conversation user interface may display a tray that is configured to save conversation items. The conversation item may then be saved to the tray when the user moves the item to the tray. In another example, a conversation item may be tagged by associating the conversation item with a displayable indicator (e.g., a flag). In some instances, the conversation user interface may include a timeline bar with marking indicating locations of conversation items that have been tagged. If the smart device 102 receives a selection of one of the markings from a user, the conversation user interface may navigate to the location in the conversation where the conversation item is located.

Figure 16:
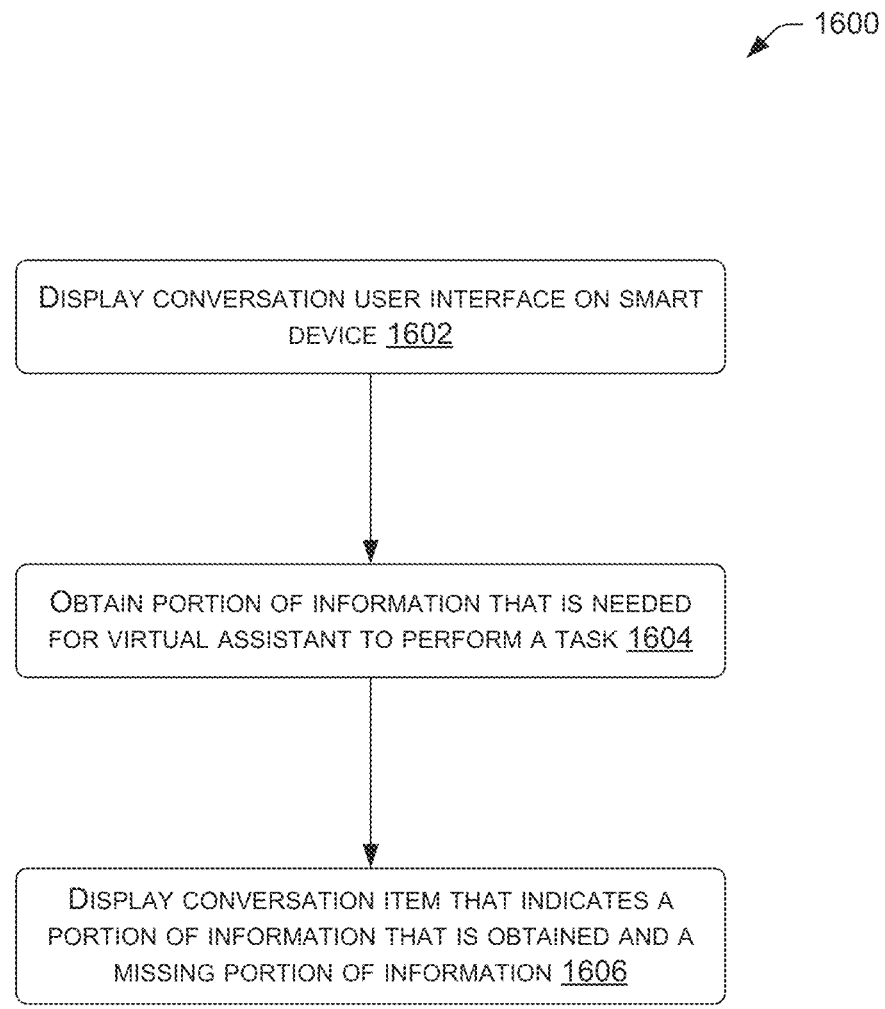
FIG. 16 illustrates an example process for displaying a conversation item within a conversation user interface that indicates a portion of information that is missing for a virtual assistant to perform a task.

FIG. 16 illustrates the example process 1600 for displaying a conversation item within a conversation user interface that indicates a portion of information that is missing for a virtual assistant to perform a task.

At 1602, the smart device may display a conversation user interface on the smart device 102 to enable a conversation between a user of the smart device 102 and a virtual assistant implemented at least in part on the smart device 102.

At 1604, the smart device 102 may obtain a portion of information that is needed for the virtual assistant to perform a task. For example, the virtual assistant may interact with the user to obtain the portion of the information. Alternatively, or additionally, the virtual assistant may obtain the portion of the information through an information source, such as a user profile, data base associated with an airline, etc.

At 1606, the smart device 102 may display a conversation item within the conversation user interface that indicates that the portion of the information has been obtained and indicates that another portion of the information is needed for the virtual assistant to perform the task (e.g., missing portion). In some instances, upon displaying the conversation item, the smart device 102 may receive the missing portion of the information from the user through the conversation user interface.

Figure 17:
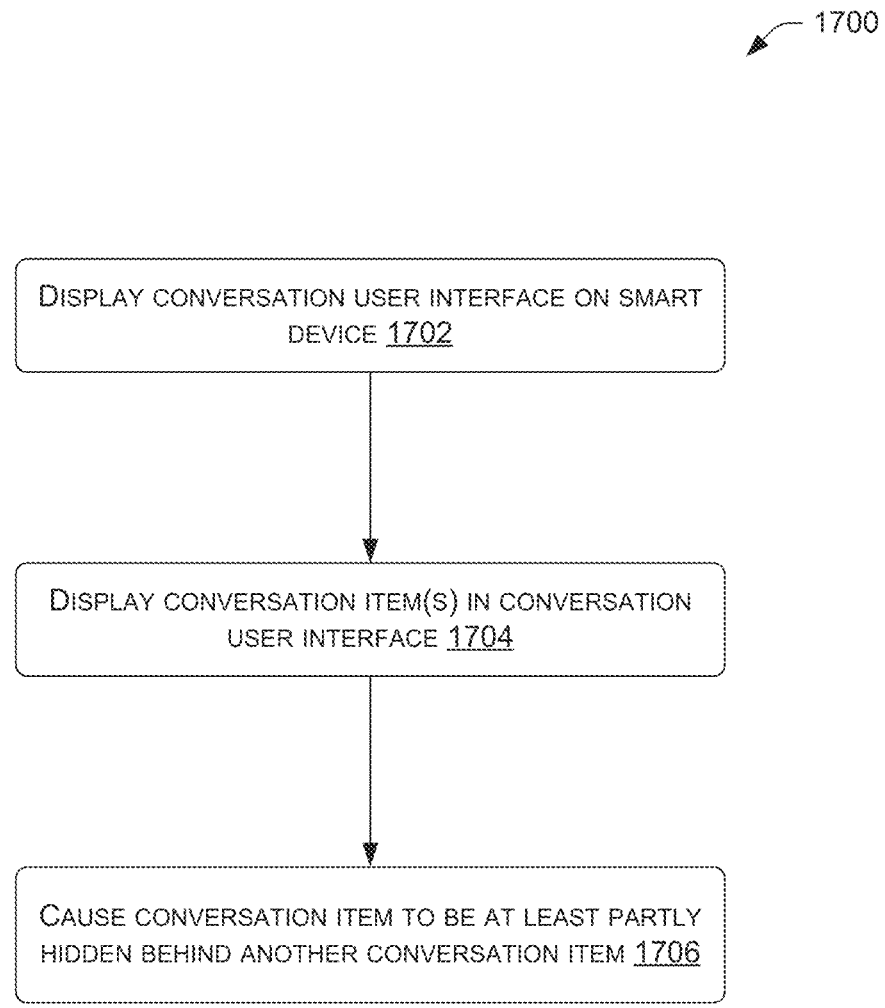
FIG. 17 illustrates an example process for hiding a conversation item of a conversation user interface behind another conversation item.

FIG. 17 illustrates the example process 1700 for hiding a conversation item of a conversation user interface behind another conversation item.

At 1702, the smart device 102 may display a conversation user interface on a smart device 102 to enable a conversation between a user of the smart device 102 and a virtual assistant implemented at least in part on the smart device 102.

At 1704, the smart device 102 may display one or more conversation items in the conversation user interface. Each of the one or more conversation items may represent input of the user, a response of the virtual assistant, or both.

At 1706, the smart device 102 may cause a conversation item of the one or more conversation items to be at least partly hidden behind another conversation item of the one or more conversation items. For example, a conversation item may be displayed in an overlaid manner over a least a portion of another conversation item.

CONCLUSION

Although embodiments have been described in language specific to structural features and/or methodological acts, it is to be understood that the disclosure is not necessarily limited to the specific features or acts described. Rather, the specific features and acts are disclosed herein as illustrative forms of implementing the embodiments.

What is claimed is:

1. One or more non-transitory computer-readable storage media storing computer-readable instructions that, when executed, instruct one or more processors to perform operations comprising:
   causing a conversation user interface to be presented by a smart device to enable a conversation between a user of the smart device and a virtual assistant implemented at least in part by the smart device;
   receiving an input request through the conversation user interface from the user that is received during the current conversation between the user and the virtual assistant [wherein the input from the user is open to multiple interpretations];
   identifying, by natural language processing, multiple interpretations of the input request;
   identifying contextual information that is related to the conversation between the user and the virtual assistant; and
   causing one or more contextual conversation items to be presented within the conversation user interface based at least in part on the contextual information, wherein the one or more contextual conversation items comprise a mixed response information indication item that includes a first subitem that identifies a task associated with [satisfies] one of the multiple interpretations of the input request of the user and a second subitem that identifies a second task associated with [satisfies] another of the multiple interpretations of the input request of the user, and wherein the first and second subitems are each presented partly behind the mixed response information indication item so that a portion of each subitem is hidden behind the mixed response information indication item and a second portion of each subitem is displayed; and receiving a selection of the first or second subitem to present information in the first or second subitem in the conversation user interface and to execute the task associated therewith.

2. The one or more non-transitory computer-readable storage media of claim 1, wherein the contextual information comprises at least one of a location of a user, an event associated with a user, environmental data obtained by a sensor of the smart device, a preference of the user, conversation history of the user with the virtual assistant in the current conversation, or conversation history of the user with virtual assistant in a previous conversation.

3. The one or more non-transitory computer-readable storage media of claim 1, wherein:
the contextual information comprises event information related to a future event associated with the user; and
the one or more contextual conversation items comprise information that is relevant to the future event associated with the user, the information being personalized for the user based on previous interactions of the user with the virtual assistant.

4. The one or more non-transitory computer-readable storage media of claim 1, wherein:
the contextual information comprises a portion of information that is needed for the virtual assistant to perform a task; and
the one or more contextual conversation items comprise a missing information item that indicates that the portion of the information has been obtained and indicates that another portion of the information is needed for the virtual assistant to perform the task.

5. The one or more non-transitory computer-readable storage media of claim 1, wherein:
the contextual information comprises an input mode that is currently used by the user to interact with the virtual assistant; and
the one or more contextual conversation items comprise a suggestion item that suggests an alternative input mode to the input mode that is currently used by the user.

6. The one or more non-transitory computer-readable storage media of claim 1, wherein:
the contextual information comprises collected information that has been collected during a current conversation between the user and the virtual assistant; and
the one or more contextual conversation items comprise an information item that represents the collected information in a condensed format.

7. The one or more non-transitory computer-readable storage media of claim 1, wherein the information item further represents information for a task that has been performed by the virtual assistant based on the collected information.

8. The one or more non-transitory computer-readable storage media of claim 1, wherein:
the contextual information identifies an orientation of the smart device; and
the one or more contextual conversation items are presented based at least in part on the orientation of the smart device.

9. The one or more non-transitory computer-readable storage media of claim 8, wherein the one or more contextual conversation items are scrollable in a horizontal direction within the conversation user interface when the identified orientation of the smart device is a portrait orientation.

10. The one or more non-transitory computer-readable storage media of claim 9, wherein the one or more contextual conversation items are presented on a timeline when the identified orientation of the smart device is a landscape orientation.

11. The one or more non-transitory computer-readable storage media of claim 1, wherein the one or more contextual conversation items comprise one or more option items representing options for the user.

12. The one or more non-transitory computer-readable storage media of claim 1, wherein the one or more contextual conversation items comprise one or more option items representing options for the user.

13. The one or more non-transitory computer-readable storage media of claim 1, further comprising controlling an input mode of the conversation user interface according to the contextual information.

14. The one or more non-transitory computer-readable storage media of claim 13, wherein the controlling comprises causing the conversation user interface to be presented with an input mode that is selected based at least in part on a location of the smart device, the conversation user interface being configured with the input mode as a primary mode of input.

15. The one or more non-transitory computer-readable storage media of claim 13, wherein:
the contextual information comprises location information indicating a location of the smart device; and
the controlling comprises causing the conversation user interface to be presented with an input mode that is selected based at least in part on the location of the smart device, the conversation user interface being configured with the input mode as a primary mode of input.

16. The one or more non-transitory computer-readable storage media of claim 13, wherein:
the contextual information comprises input history indicating one or more input modes that the user has previously used to interact with the conversation user interface or another user interface; and
the controlling comprises causing the conversation user interface to be presented with an input mode from among the one or more input modes that have been previously used by the user, the conversation user interface being configured with the input mode as a primary mode of input.

17. The one or more non-transitory computer-readable storage media of claim 14, wherein:
the contextual information indicates an inferred type of input mode of the user; and
the controlling comprises causing the conversation user interface to interact with the user through the inferred type of input mode of the user, the conversation user interface being configured with the input mode as a primary mode of input.

18. The one or more non-transitory computer-readable storage media of claim 17, wherein:
the inferred type of input mode of the user comprises text input; and
the controlling comprises displaying a keyboard within or proximate to the conversation user interface.

19. The one or more non-transitory computer-readable storage media of claim 17, wherein:

the inferred type of input mode of the user comprises touch input; and the controlling comprises displaying a selectable icon to receive touch input.

\* \* \* \* \*